(12) United States Patent
Breier et al.

(10) Patent No.: US 7,011,973 B1
(45) Date of Patent: Mar. 14, 2006

(54) REGULATORY SEQUENCES CAPABLE OF CONFERRING EXPRESSION OF A HETEROLOGOUS DNA SEQUENCE IN ENDOTHELIAL CELLS IN VIVO AND USES THEREOF

(75) Inventors: Georg Breier, Bad Nauheim (DE); Werner Risau, deceased, late of Butzbach (DE); by Barbara Risau, legal representative, Butzbach (DE); Volker Rönicke, Bobehnheim-Roxheim (DE)

(73) Assignee: Max-Planck-Gesellschaft zur Foerderung der Wissenschaften e.v., Munich (DE)

( * ) Notice: Subject to any disclaimer, the term of this patent is extended or adjusted under 35 U.S.C. 154(b) by 0 days.

(21) Appl. No.: 09/445,201

(22) PCT Filed: Jun. 3, 1998

(86) PCT No.: PCT/EP98/03318

§ 371 (c)(1),
(2), (4) Date: Apr. 12, 2000

(87) PCT Pub. No.: WO98/55638

PCT Pub. Date: Dec. 10, 1998

(30) Foreign Application Priority Data

Jun. 3, 1997 (EP) ............................................ 97108959

(51) Int. Cl.
*C12M 5/10* (2006.01)
*A61K 48/00* (2006.01)
*C12N 15/00* (2006.01)
*C07H 21/04* (2006.01)

(52) U.S. Cl. ...................... 435/325; 514/44; 424/93.21; 536/23.1; 536/23.2; 536/23.4; 536/24.1; 435/320.1

(58) Field of Classification Search ................. 435/325, 435/320.1; 514/44; 424/93.21; 536/23.1, 536/23.2, 23.4, 24.1
See application file for complete search history.

(56) References Cited

PUBLICATIONS

Vile et al., Cancer gene therapy: hard lessons and new courses, 2000, Gene Therapy, pp. 2–8.*
NIH, Office of Biotechnology Activities, Feb. 2, 2000, pp. 1–9.*
Eck et al., Gene–Based Therapy, pp. 77–101.*
Ema et al., A novel bHLH–PAS factor with close sequences similarity to hypoxia–inducile factor . . . , Apr. 1997, Proc. Natl. Sci., vol. 94, pp. 4273–4278.*
Anderson et al., Human gene therapy, Apr. 30, 1998, Nature, vol. 392, pp. 25–30.*
Verma et al., Gene therapy–promises,problems and prospects, Sep. 18, 1997, Nature, vol. 389, pp. 239–242.*

* cited by examiner

*Primary Examiner*—David Guzo
*Assistant Examiner*—Daniel M. Sullivan
(74) *Attorney, Agent, or Firm*—Gray Cary Ware & Freidenrich, LLP

(57) ABSTRACT

Described are recombinant DNA molecules comprising the regulatory sequences of an intron of the Endothelial Growth Factor (VFGF) receptor-2 gene (Flk-1) or of a gene homologous to the Flk-1 gene, being capable of conferring expression of a heterologous DNA sequence in endothelial cells, preferably in vivo. Vectors comprising said DNA molecules as well as host cells containing the same are provided. Also provided are pharmaceutical and diagnostic compositions comprising such recombinant DNA molecules and vectors. Furthermore, cells and transgenic non-human animals, comprising the aforementioned recombinant DNA molecules or vectors stably integrated into their genome and their use for the identification of substances capable of suppressing or activating transcription of a gene in endothelial cells are described. Described is further the use of the before described recombinant DNA molecules and vectors for the preparation of pharmaceutical compositions for treating, preventing, and/or delaying a vascular or tumorous disease in a subject. Furthermore, uses of the recombinant DNA molecules and vectors of the invention for the preparation of pharmaceutical compositions for inducing a vascular or tumorous disease in a non-human animal are provided.

22 Claims, 20 Drawing Sheets

Figure 2:
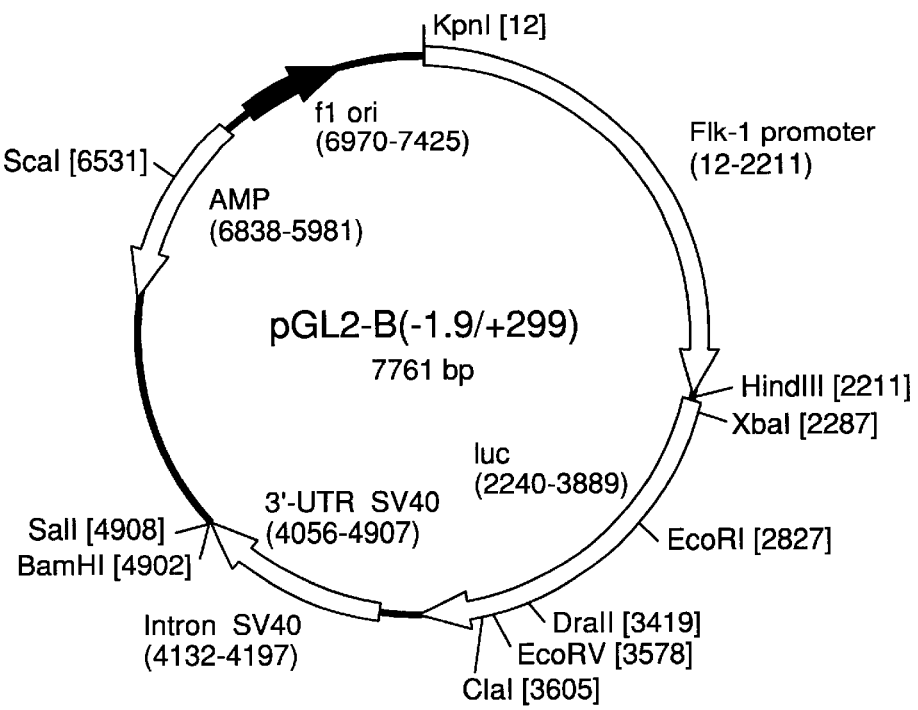

-6660 TCTAGAATAT AGAAGATAAG TTTGCGTACA ATTCAGTCCT TTGAAGACCT
     GATAAGCTTT AAGAAGGAAG ATGGGTTACA CATTGGGAAA TGGTTGCAAT
     CTGCACATGG CAGAGGCAAG AGATGCAAAT CACATTTCTT ACATACTCCA
-6510 TACAAATCTT ACAAGACTGT TTTTCTTTCT CATTTAAAAT AAGAAGACCT
     GCCAGTCTTC CCCTTATTAC TAATTACAGT CACTCTGTAT CTTTGTTGAC
     ATTGGATAGT TTTACATACT TCAACAGGCT GGTGTCATTA AAGTTGTGGT
     GGGTGGGCAC CAGAGACACG TGATTCAGAG TGGGAGGAGA TGCAGGAGAA
     ACGAGGCACA GCAGAAGCAG AAGCGAGGAA AAACACTCTC AACGTTACTA
     ACACATCGAG AGGTTCCGCA CACTAGCAAT ACGGGCTGAA TCTGACCTAA
     TCTCTGCTGT TGAAAATTTT GCCTAGCCGC ACACTAGCAA TACGGGCTGA
     ATCTGACCTA ATCTCTGCTG TTGAAAATTT TGCCTAGCCT GTCACACAAG
     TGCTGAGCAT ACAGAAAAAG GAGAGTAATT CTCTGGTTCT TTGACTAACC
     AAATAGTCTA TATCAAATTG CCTAAGATAA TGTATACATT TAGTACATGA
-6010 CTGGTTATAC CTATTCTATA TGACTATTAT TTAAATGTGA ATTTACAAGT
     GAGCATATGA AGTCCATTTT ACATGGCTAG TACATATAAC TTTTAAAAAG
     TTGGACATAG TTATATTTTT CCATTTATTT ATTTACTTTA TATCCTGATC
     ACAGACCCCC CCCTCCTCTG GATTAACTCT CTCCACTGCT TCTTACCCCT
     CCCCATCTCT CCTTCACCTC TGAGAAGGGG GGATACCTCC TGTCTTATCT
     GGTTTCAGTG GGAGAAGGAT GTATCCTAAC ACATATAATT TTTAATATCC
     TGAGTTTTTC TTTCATACAC CTTACTTATT CTATTCATTT TTCAGGAAGG
     CATGTTTAAT GTTTTTTTTT TAATTTTATG TGTACGAGTG TTTTGCCTAC
     ACAGTCATAG TGCATCGCAT ACATTTTTGC TGCCCGTAGA GATCAGAAGG
     GAGCATTGGG TTCCCTAGGA CTGGAGGCAT GAACCACCTT GTGGGTGCAG
     AGAACTGAGC CTGGGTCATC TCAAAGCATC AGGTTCTTCT TGAGTCATCT
     CACTTGCCAC TTCTCCCATT TACTGATTTT ATCTGTGTGC AGACATTCAT
     GGCCCAGTCC ACAGGTGGAA GTCAGGGACA ACCTATAGGA GTCAGTCCTC
     TCCTTCTACC GTGTGAGTCC CTGGCCTCAA ACTCAGGTTG TCGGGCTTCA

FIG. 1-1

```
        TAGCAAGAGC TTCTATTTGT TGAGCCATCT TGCTAGCCCC ACCCCATACT

ATCTTTATAA TATCTGTTTA ATTAAGACAT TCATAATGAA TTTTATTAAC

ATTCATCGTT ATCCCCTTTA CCAATTTTAC TATGTATTAA TTGCCACCCC

TTTAAATTTA ATTACTTCCT TGGCTGGGTT TTACAGGAGA GTTCCAGGAA

GCTAGATGGA GAGATGGCTC AACAGTTTAG AGCAACGGCT GTTCTTGCAG

AGGACCTAGG TTCAAGTCCT GGCACTCAGA GGTGGCTCAC AATCATCTGT

-5010   GACTTCAGTT CCAGGGGATC TGAAGAATTC TTCTGGGCTC CATGGGCATC

AACTACACAC TTGGTTCATA GACATACATG CCAGCAAATG ATTGATCCAT

ACATATGAAA TAAACCATAA ACAGAAAAAA AAAAGGAAGG TGAGGGAAGG

AAAAAAAGTT TAAAAAAAGG AAAGGAAGGA AGGAAGGGAN NNNNNNNNNN

NNNNNNNNNN NNNNNNNNNN NNNNNNNNNN NNNNTCTCTC CATACTGAAA

GATGTCCACA ATGACTAAGG GAATTTTTTT TAAAAGACAA GCACAACGTT

TTCTAGGGAT CAAACTCTAT TTGTGAGGAA GACTGGTGGT TTGAAGATTA

CATAGCAGAG TTACATCTAA CATGAGCGTG TTTCCCCTGG ATGGAAGGAG

TCTGATAACT TGTCTTTCTT TCTTAGTTAG CATCTCAGAG TCCCCCGCCT

CCCTTAACAT CCTTTTTGCA CACCATCTTT TTAGGAAAAT GGATCATTTA

TGGGGATGTA GTGATTTGTA CAAGAATGTC CCCTGTGGGC TCAGATATTT

GAATACTTAG TTCCCAGTTG GGGGAGCTTT TGTAGGGAGG TTGGGAGGCA

CAGCCTGGCA GGAGGAAGCA TGCTAGCAGC TTTGAGACTA TAAACCCTCA

TCTACTACCT TGTTCTCTTT CTGCATTGTG CTGTGTCTGA CACTGTGAGA

TTCCTGCTCC CGATGCCATG CCTGCCCGCC ATGATAGACT CCTAGCCCTC

TGGAAAGGTA ACCTCAGTGA ACTCTCTTCT ATAAGTTTCT TTGCTCCTGG
                                        HindIII (-4200)
        TGTTTTATCA CTGAAACGGA AAAGCTTGCA GGGAGGTAGG AGGCAGCCTG
```

FIG. 1-2

BstEII (-4100)

```
       TGGCGTTGAT TCAATGCACC TGGCCTTATC CTCGGATGAG ATCGGTCACC
       AGTCAAAAAC TGTGAGCTTG AAGGTCTTGG GTGCTTAACA TCTATTTTTA
       CAAATCTTAT TTAGCAACTT AGAACTGTGA AATATTGGAA AGCTACTTAA
-4010  ACCTTCTAAA CTCCCTCCTC CACACTATGA GAATGTTACA TTTTCTATTC
       AGTTATTTTT GAGCAGTAAA CAGATGAATC AAGGAATATG CCCATCACAT
       CAAGAGTGCT CCTAAATGGA CTTGCTTGTT ATTCATTTAC AGTGTGGCCC
       CTTGACTTTC ATCGGCACTC CTAGCAGAAA ACAAAATCCG CCAGATGGAG
       CTGGAGAGAT GGCTCAGCTG TTAAGAATAC TTATCCCTAC ACAGGCCCTG
       GAGCCAGTTC CCAGCACCCA CACGGTGGCT CACAACCATC TGTAACTCCA
       GTTCTAGGAG ACCCGACTCC CTCTTCTGTC TGAAAACACC AGGCACGCGT
       GCGGTCTACA TACAAACATG AAAGCAAAAT ACACACATTA CATAAATAAA
       TCTTAAAAAA TGATTCGGGG TGGGGGAAGG AAAAAAAGG ATGTTAGAAA
       ATCGATGTAA CTGTTTTTTC CTTTTGCACA GATCTAAGTT AGGGAAGGAG
       AACATTCTCT TACCATCGAA ATAATTGTT TTCATTGCCC CCAAGTCTGC
       TAATAGAGCT TGCTACCTTC ATGGCTGTCG TAAGGATGAG GCAAAGATGG
       ACTTCAGCTT TCAGACTGTG TCTGCTCAAA TGTTGGCTAC TCCTGTTTTC
       TGACCCCCTT CTCTGGTGCA ATGTGGACTT TCAATTAATT TCCCTGCATC
       TTTTACATAT TTGATTTAAA AAATATTTTA TTTTATGTAA TTGTATGTAT
       ATGCATGTCA ATAAGCATAT GTGTGTGTGT TTCCATGGAA ACCAAGGCAA
       CAGATTTTCC AGAGCTGTAG AAATGGGCTG TGAGACGCCC ACTGTGGGTG
       TTCGGAACCA AACTCGGGTC CTGTGGAAAG ACAGCGAGCA CCCATAATGC
       AGAGGTATCT CTCAGATTTT ACTTTAAAAT TTCAATTTTC TTTTTTTTTT
       TTAAAGTTCC AAGTAACTAT AGGAAAGTAC ATGGGTATAT AGATCCCCAG
-3010  TACCAAGATT CTTCCTTTGC AGGTAGCACA ACTTGGTTTG TTTCACATAA
       AGAATGGAAA GTCATTAAAA CACTCATCAC ACTGTAAAGT AGAATTGAAC
       TCTGACAGAA CAAGCGAAGT GAGTCTGACT TCCAGGTAAC TGAGCCTTCT
```

FIG. 1-3

```
      TTTCCTCCTA AAGACACAAG CCATACACAG AGTAAAATAA ACTTGGGCAT

GGTGAGAAGG AAACAACGCA GGAGGGCTAG CCAAGTCTGA GAGTCGTGAG

TGTGCTCGGT TTATAAACGG AGCCCACCTT GCCAGCGAGG TAGTCACATG

CTCTGCTAAA CAGAAACTTA AGAAAACACT TACACGAAGC AAACATGGGG

AAGTGCCATG CAAGCATGTG ACTGACTGGT GGCAATGACC GAAACCACAG

CAGCCACTAG AAAAGGAAGG GTAGTGCGCC ACACTGTAGT TGTGAAAATG

AACTTATTCA TTTATTTTGA AAAACGTGTA AGAAGCAAAG ATGTCTTCTT

TCCCACCTAC CTTTGCGGCA GGCGAGCACT TCCTGGAATT TATAAAGTGC

GATCTTTCTG GGGACTTCTC ATAACATTTC CTACTGCTCA TCTATGTCTG

TGTCAAATAG AGAATGCTCT TGAACAAGTG TGTGTGTGTG TGTGTGTGCG

CGCGCACGCG CACTCACTCC TGCTCTGTTG AGGTCCAGTT TTGATGGTCC

CGCCAGAGGT ATATTTGAGT ATCATTTCTC AAGAGCTTCA GCTGGGAGAC

ACTGCCTCTT ACTGGCCTGA AGGTCACTAG CTGATTCATC TCCGTTTGGG

CTGGCGCGCC TTGGGGATCC TCCTATCTCT CCTTCCCCAG TGCTGGGATA

ACAAGGTTGG CACCACATGA GCCTTTTAAA ATGTGAGTTT GGAAGCTCAA

ACGCAGGTTT TCATGCTTGC ACTGAAACTT CACAAGCTGA ACCGTCTCCC

TCTCCTTCCC TCTCTTTTTT CCTTTTCTTC TTCCTTTTTA AAACACATCT

-2010 TGTCTTTAAA AAAAAAAAAA GGCCCAAAAC AAGTGTAAAG TATTTCCCTA

TGTGTGTGGA GGGAGGGAGT ATAGGAGGCT GATTTCACTG AGATCCTGTT

AAATTTGGGT GCCATAGCCA ATCAAAGACG CATCGTTTCC TCTAAGAATT

CTAAATGGGG CGATTACCAC GGGCCTGCAG GTTCTGGTTT GTATTAGAGG

AGACACTGTC TTCTTAAGTA AAACATAGAA GGGGAAGTGT CCAGAATTGT

AAATAAGGCT TCGAGAGAAG CCTTGTCTGG CCACCGGGAT GGAGAAGACC

TACCTTCGCC TATCCAGGAT CCATCGTCCC TCCCTCTACC CAGATCTGAC

AGCCCTCCTT GGCTCTTTTG CTGAGGTTTG TTTGAGTTTG TTTTACTCTC

TGCAAGAGAA GTTTCCTTAA ACATTCTACC CTGTTCACAA GTAAATACAC

CTCTTAGCTA AGAGGCCACA CACCCAGGGG GAACACCGAT AAAAAGAACA
```

FIG. 1-4

```
        AGCCAGAACC TTCAGAACGC TGTCGATAGG TACACCAAGC AGCCTTCATA
        CGGAGTTTTC ATTCGTGAGG AGCTGAATAT ACAACAAAGC TAAATGTGAG
        CAGACCAGGC ATGCCTCTGC TAAATGAGGA TGCCCACACC AAACATGCCC
        AAGATCTTCA AGTATAATTT TATTATATAG ATTCGCTATG TGTTGACATG
        TTTTTATAGT GAACCTGGAT TTTACAAACC CTCCTGGTTT GCCACCTGCT
        TCTGGCACCA TACTTGAGGC TTAGGCACGT GATAAGGAG  CATGCCTGTT
        TCCCCCCTTA TTTTTTTTAA AGAAAAGCAC CATGTTACAT CATTAATCAT
        GCATATCAGT GTAGTTTAGA TCCGATGTAG AGACAATAAT CTTATCTCTT
        TGTCTGGCTG AAAGACTGTC CTTTAAACTA TCATTCTAAA TGCATTTGGT
        TTTTGCCAGG AGTAAAACAT GTCACAAGAT ATTTGTTGTC ATTTCCCAGG
-1010   CGTGGAAGGA AAGGAATGGA AAGAAAACCA GGGGTGAAGG CTGCTGTTCC
        TCTCTAGTCG CTACTTGAAG TCTACATAGC TGGGGGGGGG GGGGGGACTG
        TTCACATGGG ACCGGTTTCC TCTTTGTTCC TACACTGGCG CCTCTGGCAA
        AAAACTCTCC CTTCTCTTCC CCCCAAGCAT ATCTTGGCTG AAAGGTCAGC
        TCTGAAAAGG GGCCTGGCCA AGTTACTGT  AGGGGACCGT GGTCATGGAA
        CTGGGTAAAC AAAAGCACTC TAGCAGCCAC TGGAAAAGGA CCGGGGGCTC
        TTCTCTGTGC ATTTGCCCTG GAACCCTGAC CACCGCCAGC TCCCTGCATC
        TCCTTGCTAT GGGTTTTCTG GACCGACCCA GCCAGGAAGT TCACAACCGA
        AATGTCTTCT AGGGCTAATC AGGTAACTTC GGACGATTTA AAGTTGCCAG
        ATGGACGAGA AACAGTAGA  GGCGTTGGCA ACCTGGATAA GCGCCTATCT
-510    TCTAATTAAA ACATTCAGAC GGGGCGGGGG ATGCGGTGGC CAAAGCACCA
        TAAAACAAAA CTTCCAAGTA CTGACCAACT CACTGCAAGT TTGTGCCCCG
        AGTACATCTA GGTTCAGGGG TTCTTGTCTT CATGCTCCCA ACTGCGGGCG
        GATTTTTGGT CCCTTGGGAC TTTCAGTGCA GCGGCGAAGA GAGTTCTGCA
        CTTGCAGGCT CCTAATGAGG GCGCAGTGGG CCTCGTGTTT CTGGTGATGC
        TTCCCAGGTT GCTGGGGGCA GCAAGTGTCT CAGAGCCCAT TACTGGCTAC
        ATTTTACTTC CACCAGAAAC CGAGCTGCGT CCAGATTTGC TCTCAGATGC
```

FIG. 1-5

```
        GACTTGCCGC CCGGCACAGT TCCGGGGTAG TGGGGGAGTG GGCGTGGGAA

ACCGGGAAAC CCAAACCTGG TATCCAGTGG GGGGCGTGGC CGGACGCAGG

GAGTCCCCAC CCCTCCCGGT AATGACCCCG CCCCCATTCG CTAGTGTGTA
                            +1 (transcription start)
 -10    GCCGGCGCTC TCTTTCTGCC CTGAGTCCTC AGGACCCCAA GAGAGTAAGC

TGTGTTTCCT TAGATCGCGC GGACCGCTAC CCGGCAGGAC TGAAAGCCCA

GACTGTGTCC CGCAGCCGGG ATAACCTGGC TGACCCGATT CCGCGGACAC

CGCTGCAGCC GCGGCTGGAG CCAGGGCGCC GGTGCCCCGC GCTCTCCCCG

GTCTTGCGCT GCGGGGGCGC ATACCGCCTC TGTGACTTCT TTGCGGGCCA
                                              VRE
        GGGACGGAGA AGGAGTCTGT GCCTGAGAAC TGGGCTCTGT GCCCAGCGCG

AGGTGCAGGA TGGAGAGCAA GGCGCTGCTA GCTGTCGCTC TGTGGTTCTG

CGTGGAGACC CGAGCCGCCT CTGTGGGTAA GAAGCCCACT CTTTAGTAGT

AAGGCGGAGA AGTAGGGTGC GGGCGGAGAG TGGGAATAGA AGAGGACCTA

ACTCGTAGAG CTCTAGAGAC CCTCCTCCCT TGGGTGTTCT TTCACTTACC

+490    AATGGGGAAA CTGAGGTTCA AAGACTCTTC CGAAATGACT CAGCCAGGAT

TCTACTCTCC CCCGGGCATC GGTTGGAGCG TGTCCTGCGG AGCCGTCACA

GCCCCTGGCG CTAGGTAGGC AGGAGTGGAA AGGCGGCCTG AGCCGGGGCA

GGAGATGCTC CCACTGGCAG GAACAGGCGG TCAAACGCTG GGAAGCCAGC

TCAAGCCAAG CGGCCCGGCT GGCATCAATC ACTCGGTGCT GTTGCCCACC

GCCCTAGTGG GGGGCAGGGA ATCCGCCTCT GGCTCCGCTC CCCTTTAGCT

CCAGCGTGTA AGCGCACGGA CTATGTGAGG GTAGGTCTCT TCATAGAGCA

ACACTTTCCT CCCTCAACTT TCTTTGATGC AGAATGCTAT TTTTGCTGGT

AGGAGGAAGA CGCGGCTTTC TCTTCTGTGA CAGCTTCTCC AGGTGTATTA

AACTAAATAA CTCTCCACTT ACCGACTCCA AAGCGCTGGT CCTGGGGTAA

+990    ACTCTGAAAG TCTCAGAAAC TCTTGAGCTT GGCACCTAGT TATAGGTCAC

TTTTCTTGTT TTAAAATGCC CTCTGCTTCA AGGTTAGGCC CACACTCGCT
```

FIG. 1-6

```
CTTGGGCTTT TGTGCAATAA TTTCCCTTCC CTTCCCTTCC CTTCCCTTCC
CTTCCCTTCC CTTCCCTTCC CTTCCCTTCC CTTCCCTTTC CCTCTTCCTT
TTCCTCCTCC TCTTCCTCCT CTATTTCTCT GTCATTTCCT TTTTGAAGCC
ACAGTTTGCA GATTTCCAAT CTCCACCCAT TGGAGAATGG AGAATCAGGA
AAAAAGAAGT CAATTCTGCA GAAACATTCC TTGCGCCCTA AGAGAATCGC
ATGGCTTAAA AGCATTGGCA CTGACATACG GCGCCAAGAT CGCCTGTCTA
GAGCTATTGA GTTTTCCTCA TAATGACTTG GTTCATCAGG CTAGCTCCAC
CACGAGTGCC CTCTTGTTCC TGAGAAGGCC GCACTCTCCC CCTTTCTGGG
AAGAGAAAGA CAGCCTGGAA CATGTGCTTG CCCTGGGTTC CATAGAGAAG
CAAGTTGCTT TAAAGCCCAG AGAATTCCTA GTGTAGCAGC TTAACAGCGT
CCCGTTCTCT GAATAAGATG GAGGTTGCCC TTTTGGAGTG TGTGACTTGC
                                      XhoI (+1600)
TTAATTGGAT TGGGCTATAA TTGGTGCCAT CCAAGTCTCG AGACAGAGCC
GCTGTTGTTT TTCCTTCTGG TCTTTGAGCG GGAAGGATAA CAGTGCACAA
ATTAATTAAT GTTGGTTATC GGATTTGAAC ATAAAAGGGC TTTTATTGTA
TAGTAGCATA TGTACCTCTT GCAGTCAGAA TGAGCTGTCT AAAGAACAGA
ACCCAAACTT GCCGATGAAA ATGAATGAGG TTTAATAAAG GCGATGGATG
AGCATTAGTC ACTGATGTAA ATCTCCAGTT ATTGATAACC TCATTGACTG
GATTTGATTG CAGACATGTA TTGGTATGGG GCATCCTTTA AAGATGAGCA
+1990 TAGCCAACGT GCCTGCACTC TAAGAGAATC TATGGCTGTA TGTTATTACA
GAGACAGTTG AGAAGCTCTT AGTGGCTCTG GCGTGTAGAT CAGCGGTAGA
GCGCTGAGGC TCTGCGCTCG CTTCCTGGCA CTGAAGAATA AAGGCCATTT
ACTGTGGTGG TGCAGTGGGC GCAGTTTGTG ACGAGTTACT ACTACATTTT
CCTCACACAT CTGCCTGACT AATGAGTTCA TCAGATGAGC GTATCCAGTG
ATTGTTTGCA GGTTAATGGT TCTCAGTCAT GTTTAGAATC TACTTATCAA
ACAAATTGTT TTCTCATTTC CTGCTTCTTC TCAAACAAAG TAAGATTCCA
TTATTGAAAG GCTTGTTTAA GAGCATTTTA ACTGCTTGCC TATGTTAGGG
```

FIG. 1-7

```
        ACAGTGACTT ATTTCATATT GACAAATATT ATGCCGATTA ATTGAATATG
        ACTACCCAGT TCTATAGCTG TCTCAGGGCA GACCAAGAGC ATCTGTGATC
        CAGTCACTTT AAATGCCATT TAAATGCAT  AATTTGTTGG TCTAGGAATA
        AACACACTGT AAAGTTTAGA ATCACGGCCC AAACACAAGT CTTTAACAAT
        GCCAACTAGC TTCTGAGATT CATTAATGTC ATTTAATTAC CAATGTTTTA
        AAAATATGTC ATTAATTACT AAATCTATAG TTGTAACAGC AACACATGTA
        CATCTTATTA AGTTGGGTAT ATTCAGGGTG GCATAGCTGT AGACTATTGC
        ACATCTGTGT TGGTGAGCCA GTGGAGAACT GCCTCCTGGC TGTTCTCAGA
        AGGCCACAGT GTCACGGCAT TGGCTATTTG CCTTGGCTCT TTGCTAATAC
        TTTATTGACA TGGCCTCATC TTCGTTCACG TTCACTTATT TGCCCAACAA
        CGTCAATGCC AGCTGAGGCC TTAGGAGTCA TCTGTTCTTA GTCAGTGCGA
        ATTAGAAAGC CTGGATGCCT GCCTGCTATT AATTAGTTAT TCTTCTCTTC
+2990   TGAGACAGAG TCTCACTGTG TGGCCCAGGC TAGTCTCAAA CTTGCGGTCC
        ATTTGTCTCA CTCATCAGAA TGCTGGGCTT CCAGGTGTGT GCACCACACT
        AGGTAGCTCG CGTTTTAAGC TAAGAGCTGG AAGATCCTGA TGTCCTTTAC
        CATGGTGGGC ATGTTACAGG TTAGTTGACT GAAAACTAGT TATCTCGCTG
        TGTAATGACC TGCAGTGGTA TGTATCTCTC AAGATGCTTT TTTGCATTTC
        AATCAGTTAG GTAACAAGTT CTTAAGTCTC CAGCTTGGTA TTGGCATGAG
        CTCAGAGCTT TGATTAATGA GTTGGGACCC CTAGCTATT  GCTCATTAGA
        CTTACACTAT TTTTAGTTTT GCTCTGAGTT TATGAATATG CATGTATGCA
        TGAACTTGGG AGATATTTTT CTTCCCCAAT TCCTTTTCCT CCATTTAAAT
        GTGCTGTCTT TAGAAGCCAC TGCCTCAGCT TCTGCAGCTC AGATACCAAA
        GGAAGTCTGG TACACAGCAT GATAAAAGAC AATGGGACGG GGTCACAGTG
        GCTCCCGTCC CTTTCAGGG  TATGGAGACG AGCTGTAGAG AGATGTCTCC
        AGGGAGTTTT CATTAATCAG CAATTTAGTC AGATCTGTGC ATCCTATGCT
        TTACAAGAAA TGTCAGTGGG CCTGAGATCA TCAGATGGAG GTTCATCGGG
        TTTCAATGTC CCGTATCCTT TTGTAAGACC TTGAAGTTGG CAACGCAGGA
```

FIG. 1-8

```
AAACAGGAAC TCCACCCTGG TGCCGTGAAT TGCAGAGCTG TTGTGTTGGT

TTGTGACCAT CTGCCCATTC TTCCTGTTAT GACAGAGCTT GTGAACTTTA

ACTGGGACTG GGGCAAAGTC AATCCCACCT TTATACAATG AATTGCTGAA

GAGGCCTTTT AAAACTTGGA GTGTGCATTG TTTATGGAAG GCTTTCCTA

BamHI (+3900)

TTGGATCCAA CTCTTTTCTA ATTTGTTTCT AGGTTTGCCT GGCGATTTTC
```
+3990 `TCCATCCCCC CAAGCTCAGC ACACAGAAAG ACATACTGAC AATTTTGGCA`
```
AATACAACCC TTCAGATTAC TTGCAGGTAA GGATTCCTTT TTGAGCCAGC

TTTCCTATGT GAAAGGACTC ATTGTTACT GAGGTCACAA CAATTTCCAC

TATTGCAGAA GTATAATAGT ATTGTTACAA TTGTTTATAA ATCATGAGAC

TTCTAAGAAC CTATTTAATA ATGAAACAAT GGAAAAGTC TTTTCAAACC

TTTGTACTCT TTTGCTGAGC CGTTTTCAAC ATGCACAAAC ATATTACACA

AATATAACAT ACACAGGAAC ACACATGAAT GCATGGGATG ATGTGCCTAA

AACTAGCATG TAATTGATAT TCACAATTAT TGATAAATTA GTAAAGCAAA

GGAATTCCTT ATGAATAGAG CTAAAATTCT ATCCATGTTC AAGTCACCCA

GAATGGCTTC TGGACATTTT TTTTTTTAGC TGTTTTCTAC AAGTGAAATT

CTGCCTGTAT TAGCAATTTA ATATCTAGCC AATAATATTC CTGACCATAT

GTCCTGTTCA GACCATGACC TTCATAATCT GGCTTGATGT TCTGGGCTTC

TTTCCCTCTT GCCAGCAAGA TGTCACGGTG TTGATGCTGG ATAAACTGAG

AAACAGAAGT TTTTCGCAAG AAGAGGACCT TGAATTTTGC TTTTCCCCTG

AGAGACAAGA AAGGAAACTT AGAGGAGGTG TAGCTGGGAG TGTGGTCATT

CATGAAAGAC CTGTTTGCAG GGCAGTGTGT TTTGCTGGGG ACAGTAATGA

GCCTAGATCG TAGTGCCATC CCAAGAGAGT GCTTGGTGGC AAAAAGAGCC

CTAGCAGCTT GTGGCAGTTG CCTCATATTT GAAGAATACT AAGAGGTCCC

CCGAATAACT CAGGGCTAGT GTTGATCATT GCATGTGGAG AGAATCCAAG

CCTCCTATCT AGGGTCTACA AAAGTAACCA ATGCCCAGTC TTTGGGGGAA
```

FIG. 1-9

```
+4990   AGCAAAACCA GAAAGCGATG ATAGCAGGAC CTGTTTATTT TCATTAAGTC
        ATGGCATTTC CAGAGACTTT GCTCCCCCTA TTCTCAGACA CAAAGCCCAC
        TTAAGATCTC CCTCTGGAGA CTGCTGGGAA CATTTCTTAA GTTCTGAAAA
        AACCCTGGAG TGATTGGGCA CAGACGATCC TGTCACTTCA TGTGAGTGCT
        AAGCTCTTTG GGTGATGACT CAGTGGGTCA CATTGTTTTA TTCATATTGA
        CTACCTTCCG TTTGCTTTGC GGAGAATGGA AGCTATAGAA GTCTGTTTGG
        TGTGGCCCTC ACAAGGCACT GTGAGCTTCT TCTCTCTGTG TGCTAACTTC
        TTACTCTCCC TTGCTTATAC CCACATAGGG ACTCTGGCTT TGTTGCTGTT
        CTTCAATGCT TCAGATGTGC CCTGGGTCCT GTCTGTCCTT CACACTTACT
        GATGCTGCCT GGAATGCTAT TCCTCCCAAT GTGCATAGGG CCAGCTCGGT
        CCAAATCCTC TCTTTTCTTT GCCTCTTTTA TATTTTCCTT CACAGTATCA
        AATCACCACA GTTTATGCAA CAAACTGAAA CTTTAAAATT GTCTGTCTCC
        TTATATTAGT GATAGGTTCC AGAAAGGCAC TGATTTTTTT TCTTCCCTGG
        TGTACACTGG GCAACTACTC TACCACTGAG CGTGATATCC TTGGTCCCTT
        AAAAGTTATC CTCTGTCCTT AATAATGCTT AGCAATCATA TTTGCTTAAA
        ATATTTATTG AATGACTGCA GGAATGAATG AATGAATGAG CTAACAGAAA
        ACTCATGACC ATGTGGGTGA TTTCCGAAAC AGAGTGTGAG ATCTTTGGTG
        GCATGTCCTT GTAGACTGTC TGCCACCAGT ATCTATCATC TTGAAGGTGA
        CTATTGAGTA GTTTATATGC ATGTGAAAAA CCAAACCTTC TATTCTCTTA
        CTCATAGCCT CTCTTAATCA TAGCCCTGTG GCATGGAGTG TACCATTGAT
+5990   ATCTTCCTGG AATACTTTTT CAGGGACAG CGGGACCTGG ACTGGCTTTG
        GCCCAATGCT CAGCGTGATT CTGAGGAAAG GGTATTGGTG ACTGAATGCG
        GCGGTGGTGA CAGTATCTTC TGCAAAACAC TCACCATTCC CAGGGTGGTT
        GGAAATGATA CTGGAGCCTA CAAGTGCTCG TACCGGGACG TCGAC (SEQ ID NO: 1)
```

FIG. 1-10

```
                                               GATA    PEA3
AAATGTGCTGTCTTTAGAAGCCACTGCCTCAGCTTCTGCAGCTCAGATACCAAAGGAAGTCTGGT    65
        GATA                  AP1
ACACAGCATGATAAAAGACAATGGGACGGGGTCACAGTGGCTCCCGTCCCTTTCAGGGGTATGGA   130
                         NFkB                     AP1
GACGAGCTGTAGAGAGATGTCTCCAGGGAGTTTTCATTAATCAGCAATTTAGTCAGATCTGTGCA   195
        STAT                    SCL/TAL-1
TCCTATGCTTTACAAGAAATGTCAGTGGGCCTGAGATCATCAGATGGAGGTTCATCGGGTTTCAA   260
  Ets-1 GATA                          Ets-1
TGTCCCGTATCCTTTTGTAAGACCTTGAAGTTGGCAACGCAGGAAAACAGGAACTCCACCCTGGT   325
                                    SCL/TAL-1 Ets-1
GCCGTGAATTGCAGAGCTGTTGTGTTGGTTTGTGACCATCTGCCCATTCTTCCTGTTATGACAGA   390

GCTTGTGAACTTTAACTGGGACTGGGGCAAAGTCAATCCCACCTTTATACAATGAATTGCTGAAG   455

AGGCCTTTTAAAACTTGGAGTGTGCATTGTTTATGGAAGGGCTTTCCTATTGGATC            511
```

FIG. 12

REGULATORY SEQUENCES CAPABLE OF CONFERRING EXPRESSION OF A HETEROLOGOUS DNA SEQUENCE IN ENDOTHELIAL CELLS IN VIVO AND USES THEREOF

The present invention relates to recombinant DNA molecules comprising the regulatory sequence(s) of an intron of the Vascular Endothelial Growth Factor (VEGF) receptor-2 gene (Flk-1) or of a gene homologous to the Flk-1 gene, being capable of conferring expression of a heterologous DNA sequence in endothelial cells in vivo. The present invention also relates to vectors comprising said recombinant DNA molecules as well as to host calls transformed with such recombinant DNA molecules or vectors. The present invention additionally relates to pharmaceutical and diagnostic compositions comprising such recombinant DNA molecules, vectors or cells. Furthermore, the present invention relates to cells and transgenic non-human animals, comprising the aforementioned recombinant DNA molecules or vectors stably integrated into their genome and their use for the identification of substances capable of suppressing or activating transcription of a gene in endothelial cells. The present invention also relates to the use of the before described recombinant DNA molecules and vectors for the preparation of pharmaceutical compositions for treating, preventing, and/or delaying a vascular or tumorous disease in a subject. Furthermore, the recombinant DNA molecules and vectors of the invention can be used for the preparation of pharmaceutical compositions for inducing a vascular or tumorous disease in a non-human animal.

In the field of neuroscience and medical therapy, there is a great demand for test systems to study the function and interaction of gene products, the malfunction or expression of which cause vascular and or tumorous diseases. Such systems would also be suitable for drug development against such diseases. A prominent example for gene products involved in vascular diseases are antigenic growth factors and their endothelial receptors which play a major role in the formation of the embryonic vascular system and in certain angiogenesis-dependent diseases, such as solid tumor growth or retinopathy. The Kinase-insert Domain-containing Receptor/fetal liver kinase-1 (KDR/Flk-1) in the following referred to as Flk-1 and Flt-1 are high affinity signaling receptors for the endothelial mitogen, vascular endothelial growth factor (VEGF) (Connolly, J. Clin. Invest. 84 (1989), 1470–1478; Leung, Science 246 (1989), 1306–1309). Through interactions with its receptors, VEGF plays critical roles in growth and maintenance of vascular endothelial cells and in the development of new blood vessels in physiologic and pathologic states (Aiello, New Engl. J. Med. 331 (1994), 1480–1487; Shweiki, Nature 359 (1992), 843–845; Berkman, J. Clin. Invest. 91 (1993), 153–159). The patterns of embryonic expression of VEGF suggest that it is crucial for differentiation of endothelial cells from hemangioblasts and for development of blood vessels at all stages of growth (Jakeman, Endocrinology 133 (1993), 848–859; Breier, Development 114 (1992), 521–532). Among many potentially angiogenic factors, VEGF is the only one with patterns of expression, secretion, and activity that suggest a specific angiogenic function in normal development (Klagsbrun, Current Biology 3 (1993), 699–702).

High-affinity receptors for VEGF are found only on endothelial cells, and VEGF binding has been demonstrated on macro- and microvascular endothelial cells and in quiescent and proliferating endothelial cells (Jakeman, Endocrinology 133 (1993), 848–859; Jakeman, Clin. Invest. 89 (1992), 244–253). The Flk-1 and Flt-1 have been identified as candidate VEGF receptors by affinity cross4inking and competition-binding assays (de Vries, Science 255 (1992), 989–991; Millauer, Cell 72 (1993), 835–846; Terman, Biochem. Biophys. Res. Commun. 187 (1992), 1579–1586). These two receptor tyrosine kinases contain seven similar extracellular immunoglobulin domains and a conserved intracellular tyrosine kinase domain interrupted by a kinase insert (de Vries, Science 255 (1992), 989–991; Matthews, Proc. Natl. Acad. Sci. U.S.A 88 (1991), 9026–9030; Termnan, Oncogene 6 (1991), 1677–1683); they are expressed specifically by endothelial cells in viva (Millauer, Cell 72 (1993), 835–846; Peters, Proc. Natl. Acad. Sci. USA 90 (1993), 7533–7537; Yamaguchi, Development 118 (1993), 489–498). In situ hybridization in the developing mouse has demonstrated that Flk-1 is expressed in endothelial cells at all stages of development, as well as in the blood island in which endothelial cell precursors first appear (Millauer, Cell 72 (1993), 835–846). Flk-1 is a marker for endothelial cell precursors at their earliest stages of development (Yamaguchi, Development 118 (1993), 489–498).

The vascular endothelium is critical for physiologic responses including thrombosis and thrombolysis, lymphocyte and macrophage homing, modulation of the immune response, and regulation of vascular tone. The endothelium is also intimately involved in the pathogenesis of vascular diseases such as atherosclerosis (Ross, Nature 362 (1993), 801–809). Although a number of genes expressed in the endothelium have been characterized (Collins, J. Biol. Chem. 266 (1991), 2466–2473; Iademarco, J. Biol. Chem. 267 (1992), 16323–16329; Jahroudi, Mol. Cell. Biol. 14 (1994). 999–1008; Lee, J. Biol. Chem. 265 (1990), 10446–10450), expression of these genes is either not limited to vascular endothelium (e.g., the genes encoding von Willebrand factor endothelin-1, vascular cell adhesion molecule-1), or is restricted to specific subpopulations of endothelial cells (e.g., the gene for endothelial-leukocyte adhesion molecule-1). Flk-1 (also known as VEGF-receptor 2) is expressed in endothelial cells during embryonic and postnatal development. The Flk-1 receptor is the first endothelial receptor to be expressed in endothelial cell precursors during embryonic vascular development. Gene targeting experiments in transgenic mice have demonstrated that this receptor is essential for endothelial cell differentiation (Shalaby, Nature 376 (1995), 62–66). Furthermore, in a variety of tumors, Flk-1 receptor expression is reinduced in the tumor vasculature, and it has been shown that signaling via the Flk-1 receptor is required for tumor vascularization and growth (Millauer, Nature 367 (1994), 576–579).

Recently, in vitro studies with the upstream region of the human Flk-1 gene (Patterson, J. Biol. Chem. (1995), 23111–23118) showed that DNA fragments located in the 5' flanking region of the human Flk-1 gene mediate expression of a reporter gene.

For studying all aspects of genes involved in vascular diseases such as atherosclerosis, however, the system described by Patterson, supra, suffers from several drawbacks. For example, promoter activity of the 5'-flanking region used by Patterson was also observed in cell types which do not express the Flk-1 gene naturally. Furthermore, the promoter fragment employed in Patterson, supra, was not shown to be expressed in vivo in its natural background. In order to specifically suppress or confer endothelium specific gene expression and for the development of endothelium specific drugs, however, one needs test systems which closely resemble the regulation of the Flk-1 expression in vivo since otherwise non-informative or even false positive results may be obtained.

Thus, the technical problem of the present invention is to provide means and methods that allow the modulation of gene expression specifically in endothelial cells in vivo, preferably at all stages of development.

The solution to this technical problem is achieved by providing the embodiments characterized in the claims.

Accordingly, the invention relates to a recombinant DNA molecule comprising:

(a) a first regulatory sequence of an intron of the Vascular Endothelial Growth factor (VEGF) receptor-2 (Flk-1) gene or of a gene homologous to the Flk-1 gene being capable of conferring expression in endothelial cells in vivo; and (b) operatively linked thereto a heterologous DNA sequence.

In accordance with the present invention, a regulatory sequence driving the expression of a heterologous DNA sequence in substantially all endothelial cells in vivo, preferably at substantially all stages of development has been identified. Said regulatory sequence is suitable to direct the expression of a heterologous DNA sequence in the above-mentioned cells. The recombinant DNA molecule of the invention allows studying the function and interaction of proteins which are expressed in the endothelium of, for example, humans and the malfunction, and/or unregulated expression of which is supposed to be the or a causative agent of vascular and tumorous diseases. Thus, the regulatory sequences of the invention are particularly suited and useful for the engineering of transgenic cells and non-human animals which can serve as a test system for the development of drugs for the treatment of vascular and tumorous diseases of endothelial origin.

In the context of the present invention the term "a first regulatory sequence of an intron of the Flk-1 gene" means a nucleotide sequence of the first intron of the a murine Flk-1 gene including the regulatory sequences which are capable of conferring the specific expression of a heterologous DNA sequence in endothelial cells, preferably at all stages of development.

The high affinity receptor for vascular endothelial growth factor (VEGF), Flk-1, is the first endothelial receptor to be expressed in angioblast precursors, and its function is essential for the differentiation of the hemangioblastic lineage. In accordance with the present invention cis-acting regulatory elements of the murine Flk-1 gene have been identified that mediate endothelial specific expression of a reporter gene in transgenic mice. Sequences within the 5'-flanking region of the Flk-1 gene, in combination with sequences located in the first intron, specifically and reproducibly targeted transgene expression to endothelial cells of the embryonic vasculature. These sequences were capable of targeting expression of the heterologous DNA sequence to angioblasts during early stages of vascular development and also to the vasculature of postnatal mice. The regulatory sequences located in the first intron also functioned as an autonomous endothelium-specific enhancer when fused to the heterologous herpes simplex vinus-thymidine kinase promoter. This Flk-1 intron enhancer contains several potential binding sites for transcription factors of the Ets and GATA families. Sequences of the Flk-1 promoter contributed to a strong, complete and reproducible endothelial cell-specific gene expression in the embryo and are essential for expression in the yolk sac.

Figure 4A:
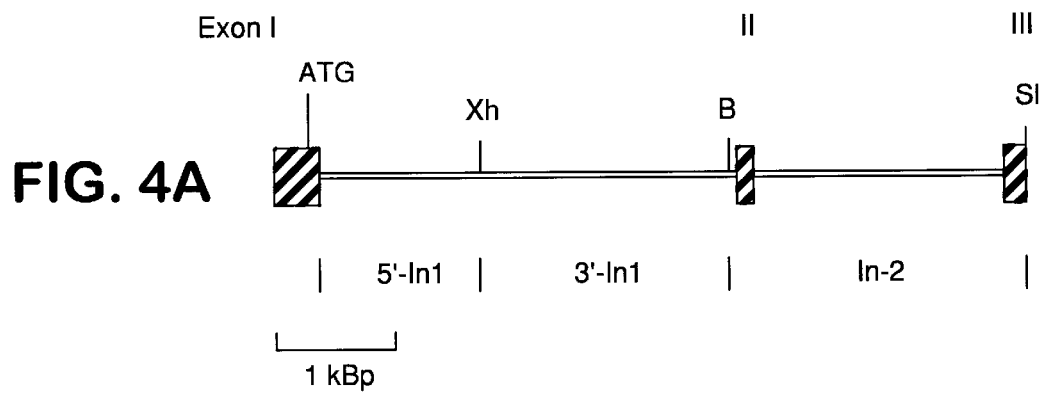

In order to characterize cis-acting regulatory sequences contained in the Flk-1 gene, recombinant bacteriophage lambda clones containing mouse genomic DNA (Mouse strain 129/Sv) have been isolated encompassing a 21 kilo base pair (kb) region of the mouse Flk-1 gene, contained in the DNA insertions of λ phages 6 and 16, including approximately 15 kb of 5' flanking sequences, exons 1, 2 and 3, and introns 1 and 2 (FIG. 4A). The DNA sequence of a 12.8 kb region spanning from position 6.65 kb (the affixes − and + refer to the nucleotide position relative to the transcriptional start site as shown in FIG. 1 which corresponds to nucleotide position 6661 of SEQ ID NO: 1) to position +6.15 (located in the third exon) was determined (SEQ ID NO: 1). Reporter gene studies were performed in order to characterize regulatory cis-acting elements of the Flk-1 gene. Initial studies focused on the role of 5' flanking sequences of the Flk-1 gene ("Flk-1 promoter") in mediating endothelium-specific expression in cultured bovine aortic endothelial (BAE) cells (Rönicke, Circulation Research 79 (1996), 277–285). In these studies, it was found that a promoter fragment ranging from −624 to +299 mediated high expression of the luciferase reporter gene following transient transfection in BAE cells. Experiments with transgenic mouse embryos performed in accordance with the present invention revealed, however, that the murine promoter DNA fragments were not sufficient to mediate endothelium-specific reporter gene expression in vivo. Surprisingly, however, when a Flk-1 promoter fragment (ranging from, e.g., −624 to +299 bp) was combined with a 2.3 kb fragment of the first Flk-1 intron, endothelium specific expression of a lacZ reporter gene in mouse embryos was obtained. Thus, the first intron (nucleotides 7027 to 10642 of SEQ ID NO: 1) of the mouse Flk-1 gene is essential for endothelium specific gene expression. In particular, a DNA fragment (see FIG. 12) comprising nucleotides 10094 to 10608 of SEQ ID NO: 1 was shown in accordance with the present invention to be sufficient to direct the expression of a heterologous DNA sequence into endothelial cells; see Example 8. This is a novel finding because the sequences described in previous publications (Patterson, supra; Rönicke, supra) are, in contrast to the expectations and interpretations of the prior art, not sufficient to mediate endothelium-specific expression in vivo. These results obtained in accordance with the present invention demonstrate that the regulatory sequences located in the intron of the Flk-1 gene mediating endothelium-specific expression can be used to direct expression of heterologous genes in the vasculature.

The genomic DNA of the murine Flk-1 gene comprising the intron regulatory sequences can be obtained from liver of mouse strain 129/SV, or, for example, by screening a phage library of liver genomic DNA in the vector λFixII (Stratagene, La Jolla. Calif.) generated by conventional methods known in the art.

The term "regulatory sequence of a gene homologous to the Flk-1 gene" also includes promoter regions and regulatory sequences of a gene from another species, for example, humans and other mammals which is homologous to the Flk-1 gene of mouse and which confers the same or substantially the same expression pattern. Such regulatory sequences are characterized by their capability of conferring expression of a heterologous DNA sequence specifically in endothelial cells in vivo, preferably at all stages of development. Thus, according to the present invention, regulatory sequences from other species can be used that are functionally homologous to the regulatory sequences of the intron of the Flk-1 gene from mouse, or regulatory sequences of genes that display a substantially identical pattern of expression, in the sense of being expressed in the endothelium, preferably at all stages of development.

It is possible for the person skilled in the art to isolate by employing the known Flk-1 gene from mouse, corresponding genes from other species, for example, humans and other mammals. This can be done by conventional techniques known in the art, for example, by using Flk-1 gene sequences as a hybridization probe or by designing appropriate PCR primers. It is then possible to isolate the corresponding regulatory sequences by conventional techniques and test them for their expression pattern. For this purpose, it is, for instance, possible to fuse the regulatory sequences to a reporter gene, such as the luciferase or green fluorescent protein (GFP) encoding genes and assess the expression of the reporter gene in transgenic animals, for example in mice. The partial nucleotide sequence of the human Flk-1 gene may be obtained from Genbank Acc. No. X89776; Patterson, supra; Terman, Biochem. Biophys. Res. Comm. 187 (1992), 1579–1586; Genbank Acc. No. X61656. The present invention also relates to recombinant DNA molecules comprising regulatory sequences which are substantially identical to that of the Flk-1 intron or to an intron of a homologous gene or to fragments thereof and which are able to confer specific expression in endothelial cells, preferably at all stages of development in mouse or other mammals.

Such regulatory sequences differ at one or more positions from the above-mentioned regulatory sequences but still have the same specificity, namely they comprise the same or similar sequence motifs responsible for the above described expression pattern. Preferably such regulatory sequences hybridize to one of the above-mentioned regulatory sequences, most preferably under stringent conditions. Particularly preferred are regulatory sequences which share at least 85%, more preferably 90–95%, and most preferably 96–99% sequence identity with one of the above-mentioned regulatory sequences and have the same specificity. Such regulatory sequences also comprise those which are analogues or derivatives, for example by way of nucleotide deletion(s), insertion(s), substitution(s), addition(s), and/or recombination(s) and/or any other modification(s) known in the art either alone or in combination in comparison to the above described nucleotide sequence. Methods for introducing such modifications in the nucleotide sequence of the regulatory sequences of the invention are well known to the person skilled in the art and described, for example, in Sambrook (Molecular cloning; A Laboratory Manual, Second Edition, Cold Spring Harbor Laboratory Press, Cold Spring Harbor N.Y. (1989)). All such fragments, analogues and derivatives of the regulatory sequence of the invention are included within the scope of the present invention, as long as the essential characteristic regulatory properties as defined above remain unaffected in kind. It is also immediately evident to the person skilled in the art that further regulatory sequences may be added to the regulatory sequences of the invention. For example promoters, transcriptional enhancers and/or sequences which allow for induced expression of the regulatory sequences of the invention may be employed. A suitable inducible system is for example tetracycline-regulated gene expression which is described by, e.g., Gossen (Proc. Natl. Acad. Sci. USA 89 (1992), 5547–5551; Trends Biotech. 12 (1994), 585–62).

The expression conferred by the regulatory sequences of the invention may not be exclusively limited to the above-described specificity but may also occur in, e.g., neuronal cells, including neural retinal progenitor cells at all or different stages of development and haematopoietic cells (Yang, J. Neurosci. 16 (1996), 6089–6099).

The term "further regulatory sequences" refers to sequences which influence the specificity and/or level of expression, for example in the sense that they confer cell and/or tissue specificity or developmentally and/or inducible regulated gene expression. Such regions can be located upstream of or comprising the transcription initiation site, such as a promoter, but can also be located downstream of it, e.g., in transcribed but not translated leader sequences.

The term "promoter" refers to the nucleotide sequences necessary for transcription initiation, i.e. RNA polymerase binding, and also includes, for example, the TATA box.

The term "in vivo" for the purpose of the present invention is used for cells in an organism as opposed to cells growing in culture (in vitro).

The term "heterologous" with respect to the DNA sequence being operatively linked to the promoter of the invention means that said DNA sequence is not naturally linked to the regulatory sequences comprised in the recombinant DNA molecule of the invention.

In a preferred embodiment said first regulatory sequence of the invention comprises a GATA-binding site, an AP-1 binding site, an SP1 binding site, site, an NFκB binding site, a STAT binding site, a Scl/Tal-1 binding site, an Ets-1 binding site, a PEA3 consensus sequence or any combination(s) thereof. A functional analysis of the first 6.5 kbp of the transcribed region of the murine Flk-1 genes lead to the identification of a endothelial-specific positive regulatory element. This regulatory sequence is located in the region between the XhoI and BamHI restriction site in the first intron of the Flk-1 gene (cf. FIG. 4A). It Is functional in both orientations since the intron enhancer was used in an antiparallel manner with respect to the Flk-1 promoter fragment in the construct referred to as 3'-In 1; see Example 2 hereinbelow. A sequence analysis of the intron lead to the identification of two potential GATA binding sites (+1927 Bp, +3514 Bp); a potential AP-1 binding site (+2210 Bp) and two PEA3 consensus sequences (+3494 Bp. +3741 Bp); see FIG. 1. As demonstrated in Example 8, the intron sequences that were sufficient for endothelium-specific expression were contained in a 510 bp fragment (nucleotides 10094 to 10608 of SEQ ID NO: 1). Several potential binding sites for known transcription factors could be identified therein (see FIG. 12), including consensus binding sites for c-ets1, PEA3 (an Ets-like transcription factor), GATA transcription factors, and Scl/Tal-1. The c-ets1 transcription factor was proposed to be involved in the early differentiation of endothelial cells from their precursors (Pardanaut Cell Adhesion and Communication 1 (1993), 151–160). In addition, c-ets1 is expressed in endothelial cells during tumor vascularization and other forms of angiogenesis in humans (Wernert, Am. J. Pathol. 140 (1992), 119–127). Proteins of the Ets family can activate transcription through a PEA3 motif (Wemert, 1992). Transcription factors of the GATA family are involved in the transcription of genes that are expressed in the hematopoietic and endothelial lineages, such as von Willebrand factor (Jahroudi, Mol. Cell. Biol. 14 (1994), 999–1008). Unlike the hematopoietic-transcription factor GATA-1, GATA-2 is expressed in both the endothelial and hematopoietic lineages (Elefanty, Blood 90 (1997), 1435–1447). Scl/Tal-1 has recently been implicated in the regulation of Flk-1 expression in Zebrafish (Liao, Genes Dev. 12 (1998), 621–626). The presence of two potential Scl/Tal-1 binding sites in the murine Flk-1 intron enhancer suggests that Scl/Tal-1 might regulate Flk-1 expression in mice. However, no direct effect of Scl/Tal-1 on Flk-1 expression has been observed so far in mice, although Scl-null mice have vascular defects (Visvader, Genes Dev. 12 (1998), 473–479). Knock out experiments performed with the above-described regulatory sequences will easily reveal which of these elements present in, e.g., the 510 bp fragment (nucleotides 10094 to 10608 of SEQ ID NO: 1) are involved in the control of the regulatory sequence and the sequential order of these elements necessary to confer endothelium specific gene expression. Of course, the regulatory sequences obtained from such studies are also within the scope of the present invention.

Preferably, said first regulatory sequence is selected from the group consisting of (a) DNA sequences comprising a nucleotide sequence as given in SEQ ID NO: 1;
(b) DNA sequences comprising a nucleotide sequence of SEQ ID NO: 1 from nucleotide 8260 to nucleotide 10560, from nucleotide 8336 to nucleotide 10608 and/or from nucleotide 10094 to nucleotide 10608;
(c) DNA sequences comprising the nucleotide sequence of the human Flk-1-intron;
(d) DNA sequences comprising a nucleotide sequence which hybridizes with a nucleotide sequence of (a), (b) or (c) under stringent conditions;
(e) DNA sequences comprising a nucleotide sequence which is conserved in the nucleotide sequences of (a), (b) and (c); and
(f) DNA sequences comprising a fragment, analogue or derivative of a nucleotide sequence of any one of (a) to (e) capable of conferring expression in endothelial cells.

Figure 4B:
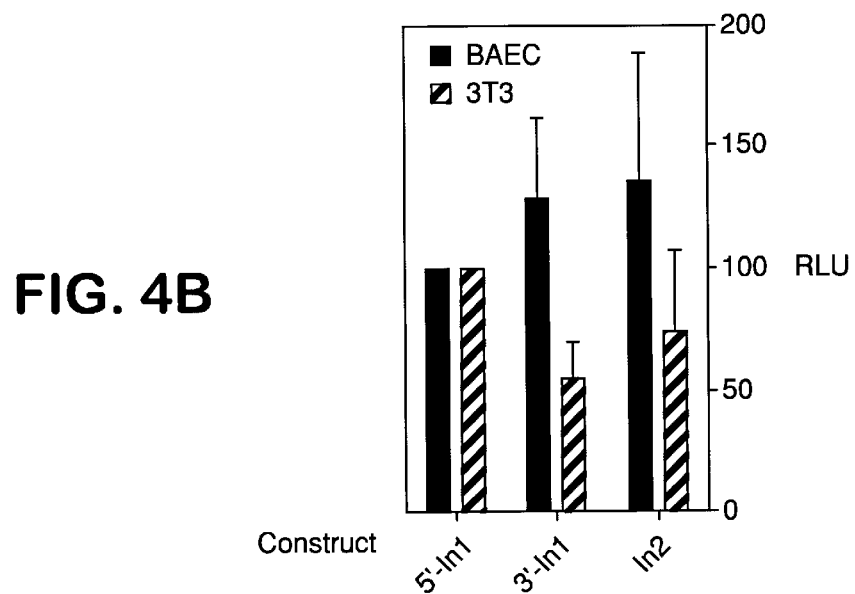

In a particularly preferred embodiment of the present invention, the regulatory sequences comprise the nucleotides 8260 to 10560, 8336 to 10608 (comprising the BamHI/XhoI fragment of the first intron (+1677 bp/+3947); see FIG. 4 and Examples 1 to 10), most preferably nucleotides 8560 to 10400 and still more preferably nucleotides 10094 to 10608 (comprising the SwaI/BamHI fragment (+3437 bp+3947 bp); see Example 8) of the nucleotide sequence as set forth in SEQ ID No. 1 or a fragment thereof, which still confers expression in endothelial cells, preferably at all stages of development.

In a further preferred embodiment of the invention the heterologous DNA sequence of the recombinant DNA molecules described above is operatively linked to further regulatory sequences. Expression comprises transcription of the nucleic acid molecule, preferably into a translatable mRNA. Regulatory elements ensuring expression in eukaryotic cells, preferably mammalian cells, are well known to those skilled in the art They normally comprise promoters ensuring initiation of transcription and optionally poly-A signals ensuring termination of transcription and stabilization of the transcript Additional regulatory elements may include transcriptional as well as translational enhancers. Preferably said further regulatory sequence is a promoter and/or a 3'-untranslated region.

Although some endothelial-specific promoters have been characterized, e.g. of the genes for von Willebrand factor (Jahroudi, Mol. Cell Biol. 14 (1994), 999–1008), Endothelin-1 (Lee, J. Biol. Chem. 265 (1990), 10446–10450), E-selectin (Collins, J. Biol. Chem. 266 (1991), 2466–2473), Tie-2 (Schlaeger, Development 121 (1995), 1089–1098), VCAM-1 (Iademarco, J. Biol. Chem. 267 (1992), 16323–16329) and endothelial NO-synthase (Zhang, J. Biol. Chem. 270 (1995), 15320–15326) these genes are neither specific for proliferating endothelium, nor necessary for endothelial cell determination. Due to the present invention these promoters can now be combined with the regulatory sequences of the invention in order to mediate endothelium specific gene expression of heterologous DNA sequences. However, other promoters can be used as well. For example, it is shown in Example 8 that the regulatory sequences of the invention conferred endothelium-specific gene expression to the heterologous herpes simplex virus-thymidine kinase (tk) promoter.

In a preferred embodiment the above mentioned promoter is a promoter of hypoxia inducible genes, genes encoding growth factors such as VEGF, PDGF or Fibroblast growth factor or their receptors or glycolytic enzymes.

In a particularly preferred embodiment said promoter comprises a DNA sequence selected from the group consisting of (a) DNA sequences comprising the nucleotide sequence as given in SEQ ID NO: 1 from nucleotide 6036 to nucleotide 6959;
(b) DNA sequences comprising the nucleotide sequence of the human Flk-1 promoter;
(c) DNA sequences comprising a nucleotide sequence which hybridizes with a nucleotide sequence of (a) or (b) under stringent conditions;
(d) DNA sequences comprising a nucleotide sequence which is conserved in the nucleotide sequences of (a) and (b); and
(e) DNA sequences comprising a fragment, analogue or derivative of a nucleotide sequence of any one of (a) to (d).

At least one of the aforedescribed DNA sequences may be preferably of human or murine origin although other sources may be employed as well. Preferably, the heterologous DNA sequence being operatively linked to the regulatory sequences is located 5' to the regulatory sequence of the invention.

In a further preferred embodiment, the heterologous DNA sequence of the above-described recombinant DNA molecules encodes a peptide, protein, antisense RNA, sense RNA and/or ribozyme. The recombinant DNA molecule or vector of the invention can be used alone or as part of a vector to express heterologous DNA sequences, which, e.g., encode proteins other than Flk-1, in cells of the blood vessel wall, i.e., endothelial cells, for, e.g., gene therapy or diagnostics of vascular diseases such as atherosclerosis. The recombinant DNA molecule or vector containing DNA sequence encoding a protein of interest is introduced into endothelial cells which in turn produce the protein of interest. For example, sequences encoding t-PA (Pennica, Nature 301 (1982), 214), p21 cell cycle inhibitor (El-Deiry, Cell 75 (1993), 817–823), or nitric oxide synthase (Bredt, Nature 347 (1990), 768–770) may be operatively linked to the endothelial cell-specific regulatory sequences of the invention and expressed in endothelial cells. For example, thrombolytic agents can be expressed under the control of the endothelial cell-specific regulatory sequences of the invention for expression by vascular endothelial cells in blood vessels, e.g., vessels occluded by aberrant blood clots. Other heterologous proteins, e.g., proteins which inhibit smooth muscle cell proliferation, e.g., interferon-γ and atrial natriuretic polypeptide, may be specifically expressed in endothelial cells to ensure the delivery of these therapeutic peptides to an atherosclerotic lesion or an area at risk of developing an atherosclerotic lesion, e.g., an injured blood vessel.

The endothelial cell-specific regulatory sequences of the invention may also be used in gene therapy to promote angiogenesis to treat diseases such as peripheral vascular disease or coronary artery disease (Isner, Circulation 91 (1995), 2687–2692). For example, the regulatory sequences of the invention can be operatively linked to sequences encoding cellular growth factors which promote angiogenesis, e.g., VEGF, acidic fibroblast growth factor, basic fibroblast growth factor and the like.

In a most preferred embodiment of the present invention, said protein is selected from the group consisting of Vascular Endothelial Growth Factor (VEGF), Hypoxia Inducible Factors (HIF), HIF-Related Factor (HRF), tissue plasminogen activator, p21 cell cycle inhibitor, nitric oxide synthase, interferon-γ, atrial natriuretic polypeptide and monocyte chemotactic proteins.

In another particularly preferred embodiment of the invention, said protein is a scorable marker, preferably luciferase, green fluorescent protein or lacZ. This embodiment is particularly useful for simple and rapid screening methods for compounds and substances described herein below capable of modulating the expression of genes in the endothelium. For example, endothelial cells can be cultured with VEGF in the presence and absence of the candidate compound in order to determine whether the compound affects the expression of genes which are under the control of regulatory sequences of the invention, which can be measured, e.g., by monitoring the expression of the above-mentioned marker. It is also immediately evident to those skilled in the art that other marker genes may be employed as well, encoding, for example, selectable marker which provide for the direct selection of compounds which induce or inhibit the expression of said marker.

The regulatory sequences of the invention may also be used in methods of antisense therapy. Antisense therapy may be carried out by administering to an animal or a human patient, a recombinant DNA containing the endothelial cell-specific regulatory sequences of the invention operably linked to a DNA sequence. i.e., an antisense template which is transcribed into an antisense RNA. The antisense RNA may be a short (generally at least 10, preferably at least 14 nucleotides, and up to 100 or more nucleotides) nucleotide sequence formulated to be complementary to a portion of a specific mRNA sequence. Standard methods relating to antisense technology have been described (Melani, Cancer Res. 51 (1991), 2897–2901). Following transcription of the DNA sequence into antisense RNA, the antisense RNA binds to its target mRNA molecules within a cell, thereby inhibiting translation of the mRNA and down-regulating expression of the protein encoded by the mRNA. For example, an antisense sequence complementary to a portion of or all of the Flk-1 (KDR) mRNA (Terman, Oncogene 6 (1991), 1677–1683 and Terrnan (1992), supra) would inhibit the expression of Flk-1, which in turn would inhibit angiogenesis. Such antisense therapy may be used to treat cancer, particularly to inhibit angiogenesis at the site of a solid tumor, as well as other pathogenic conditions which are caused by or exacerbated by angiogenesis, e.g., inflammatory diseases such as rheumatoid arthritis, and diabetic retinopathy.

The expression of other endothelial cell proteins may also be inhibited in a similar manner, for example, endothelial cell proteins such as cell cycle proteins (thereby inhibiting endothelial cell proliferation, and therefore, angiogenesis); coagulation factors such as von Willebrand factor, and endothelial cell adhesion factors, such as ICAM-1 and VCAM-1 (Bennett, J. Immunol. 152 (1994), 3530–3540).

Thus, in a further preferred embodiment of the present invention, said antisense RNA or said ribozyme are directed against a gene involved in vasculogenesis and/or angiogenesis and/or tumors of endothelial origin.

In a further embodiment, the invention relates to nucleic acid molecules of at least 15 nucleotides in length hybridizing specifically with a regulatory sequence as described above or with a complementary strand thereof. This means that they hybridize, preferably under stringent conditions, specifically with the nucleotide sequences as described above and show no or very little cross-hybridization with nucleotide sequences having no or substantially different regulatory properties. Such nucleic acid molecules may be used as probes and/or for the control of gene expression. Nucleic acid probe technology is well known to those skilled in the art who will readily appreciate that such probes may vary in length. Preferred are nucleic acid probes of 17, 18, 19, 20 to 25 and 25 to 35 nucleotides in length. Of course, it may also be appropriate to use nucleic acids of up to 100 and more nucleotides in length. The nucleic add probes of the invention are useful for various applications. On the one hand, they may be used as PCR primers for amplification of regulatory sequences according to the invention. Another application is the use as a hybridization probe to identify regulatory sequences hybridizing to the regulatory sequences of the invention by homology screening of genomic DNA libraries. Nucleic acid molecules according to this preferred embodiment of the invention which are complementary to a regulatory sequence as described above may also be used for repression of expression of a gene comprising such regulatory sequences, for example due to an antisense or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a regulatory sequence of the invention. Selection of appropriate target sites and corresponding ribozymes can be done as described for example in Steinecke, Ribozymes, Methods in Cell Biology 50, Galbraith et al. eds Academic Press, Inc. (1995), 449–460. Furthermore, the person skilled in the art is well aware that it is also possible to label such a nucleic acid probe with an appropriate marker for specific applications, such as for the detection of the presence of a nucleic acid molecule of the invention in a sample derived from an organism.

Such molecules may either be DNA or RNA or a hybrid thereof. Furthermore, said nucleic acid molecule may contain, for example, thioester bonds and/or nucleotides analogues, commonly used in oligonucleotide anti-sense approaches. Said modifications may be useful for the stabilization of the nucleic acid molecule against endo- and/or exonucleases in the cell. Said nucleic acid molecules may also be transcribed by an appropriate vector containing a chimeric gene which allows for the transcription of said nucleic acid molecule in the cell. Such nucleic acid molecules may further contain ribozyme sequences which specifically cleave the (pre)-mRNA comprising the regulatory sequence of the invention. Furthermore, oligonucleotides can be designed which are complementary to a regulatory sequence of the invention (triple helix; see Lee, Nucl. Acids Res. 6 (1979), 3073; Cooney, Science 241,(1988), 456 and Dervan, Science 251 (1991), 1360), thereby preventing transcription and the production of the encoded protein.

The present invention also relates to vectors, particularly plasmids, cosmids, viruses, bacteriophages used conventionally in genetic engineering that comprise a recombinant DNA molecule of the invention. Preferably, said vector is an expression vector and/or a targeting vector. Expression vectors derived from viruses such as retroviruses, vaccinia virus, adeno-associated virus, herpes viruses, or bovine papilloma virus, may be used for delivery of the recombinant DNA molecule or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

As is demonstrated in Example 11, the Flk-1 promoter was stimulated by HIF-2α, a basic helix-loop-helix/PAS domain transcription factor related to hypoxia-inducible factor-1. HIF-2α has previously been shown to stimulate the expression of VEGF, suggesting that HIF-2α may regulate the coordinate expression of both the VEGF receptor Flk-1 and its ligand in vivo. Thus, Flk-1 gene regulatory elements described herein can be used together with HIF-2α for the elucidation of the molecular mechanisms involved in endothelial cell specification and angiogenesis, and can be used to target expression of any transgene to the endothelium. Thus, in a preferred embodiment, the vector of the invention furthers comprises a gene capable of expressing HIF-2α.

The present invention furthermore relates to host cells transformed with a DNA molecule or vector of the invention. Said host cell may be a prokaryotic or eukaryotic cell. The vector or recombinant DNA molecule of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination.

The host cell can be any prokaryotic or eukaryotic cell, such as a bacterial, insect, fungal, plant or animal cell. Preferred fungal cells are, for example, those of the genus Saccharomyces, in particular those of the species S. cerevisiae. Suitable mammalian cell lines comprise Saos-2 human osteosarcoma cells (ATCC HTB-85), HeLa human epidermoid carcinoma cells (ATCC CRL-7923), HepG2 human hepatoma cells (ATCC HB8065), human fibroblasts (ATCC CRL-1634), U937 human histiocytic lymphoma cells (ATCC CRL-7939), RD human embryonal rhabdomyosarcoma cells (ATCC CCL-136), MCF7 human breast adenocarcinoma cells (ATCC HTB-22), JEG3 human choriocarcinoma cells (ATCC HB36), A7r5 fetal rat aortic smooth muscle cells (ATCC CRL-1444), and NIH 3T3 mouse fibroblasts (ATCC CRL-1658) obtainable from the American Type Culture Collection. Primary-culture HUVEC may be obtained from Clonetics Corp. (San Diego, Calif.) and can be grown in EGM medium containing 2% fetal calf serum (Clonetics). Primary-culture human aortic and intestinal smooth muscle cells can also be obtained from Clonetics Corp. Most preferably said host cell is an endothelial cell or derived therefrom, such as BAE cells. In view of the synergistic effect of the co-expression of a recombinant DNA molecule of the invention and HIF-2α, a further embodiment of the invention concerns the above-described cells which further comprise a recombinant DNA molecule or vector containing a gene capable of expressing HIF-2α.

Moreover, the present invention relates to a pharmaceutical composition comprising at least one of the aforementioned recombinant DNA molecules or vectors of the invention, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g. by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Dosages will vary but a preferred dosage for intravenous administration of DNA is from approximately $10^6$ to $10^{22}$ copies of the DNA molecule. The compositions of the invention may be administered locally or systemically. Administration will generally be parenterally, e.g., intravenously, DNA may also be administered directly to the target site, e.g., by biolistic delivery to an internal or external target site or by catheter to a site in an artery.

It is envisaged by the present invention that the various recombinant DNA molecules and vectors of the invention are administered either alone or in any combination using standard vectors and/or gene delivery systems, and optionally together with an appropriate compound, for example VEGF, and/or together with a pharmaceutically acceptable carrier or excipient. Subsequent to administration, said recombinant DNA molecules may be stably integrated into the genome of the mammal. On the other hand, viral vectors may be used which are specific for certain cells or tissues, preferably for the endothelium and persist in said cells. Suitable pharmaceutical carriers and excipients are well known in the art. The pharmaceutical compositions prepared according to the invention can be used for the prevention or treatment or delaying of different kinds of diseases, which are related to the expression or overexpression of a given gene or genes in the endothelium.

Furthermore, it is possible to use a pharmaceutical composition of the invention which comprises a recombinant DNA molecule or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams (Proc. Natl. Acad. Sci. USA 88 (1991), 2726–2729).

Standard methods for transfecting cells with recombinant DNA are well known to those skilled in the art of molecular biology, see, e.g., WO 94/29469. Gene therapy and antisense therapy to prevent or decrease the development of atherosclerosis or inhibit angiogenesis may be carried out by directly administering the recombinant DNA molecule or vector of the invention to a patient or by transfecting endothelial cells with the recombinant DNA molecule or vector of the invention ex vivo and infusing the transfected cells into the patient. Furthermore, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., WO94/29469, WO 97100957 or Schaper (Current Opinion in Biotechnology 7 (1996), 635–640) and references cited therein. The DNA molecules and vectors comprised in the pharmaceutical composition of the invention may be designed for direct introduction or for introduction via liposomes, or viral vectors (e.g. adenoviral, retroviral) containing said recombinant DNA molecule into the cell. Preferably, said cell is a germ line cell, embryonic cell, or egg cell or derived therefrom. The pharmaceutical compositions according to the invention can be used for the treatment of all kinds of diseases hitherto unknown as being related to the expression and/or over expression of genes in the endothelium.

The present invention also relates to diagnostic compositions or kits comprising at least one of the aforementioned recombinant DNA molecules, vectors, cells and/or nucleic acid molecules and, in the case of diagnostic compositions, optionally suitable means for detection.

Said diagnostic compositions may be used for methods of detecting and isolating regulatory sequences which are a functionally equivalent to the Flk-1 intron regulatory sequences of the invention. The kits of the invention may further contain compounds such as further plasmids, antibiotics and the like for screening transgenic animals and/or animal cells useful for the genetic engineering of non-human animals, preferably mammals and most preferably mouse.

It is to be understood that the introduced recombinant DNA molecules and vectors of the invention express the heterologous DNA sequence after introduction into said cell and preferably remain in this status during the lifetime of said cell. For example, cell lines which stably express the heterologous DNA under the control of the regulatory sequence of the invention may be engineered. Rather than using expression vectors which contain viral origins of replication, host cells can be transformed with the recombinant DNA molecule or vector of the invention and a selectable marker, either on the same or separate vectors. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the heterologous DNA sequence under the control of the regulatory sequence of the invention, and which respond to VEGF and/or hypoxia mediated signal transduction. Such engineered cell lines are particularly useful in screening compounds capable of modulating Flk-1 gene expression.

A number of selection systems may be used, including but not limited to the *herpes simplex* virus thymidine kinase (Wigler, Cell 11(1977). 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) genes can be employed in tk⁻, hgprt⁻ or aprt⁻ cells, respectively. Also, antimetabolite resistance can be used as the basis of selection for dhfr, which confers resistance to methotrexate (Wigler, Proc. Natl. Acad. Sci. USA 77 (1980), 3567; O'Hare, Proc. Natl. Acad. Sci. USA 78 (1981). 1527), gpt, which confers resistance to mycophenolic acid (Mulligan, Proc. Natl. Aced. Sci. USA 78 (1981), 2072); neo, which confers resistance to the aminoglycoside G418 (ColberreGarapin, J. Mol. Biol. 150 (1981), 1); and hygro, which confers resistance to hygromycin (Santerre, Gene 30 (1984), 147) genes.

Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyly)-DL-ornithine, DFMO (McConlogue, 1987, In: Current Communications in Molecular Biology, Cold Spring Harbor Laboratory ed.). On the other hand, the person skilled in the art may also use the regulatory sequences of the invention to "knock out" an endogenous gene comprising identical or similar regulatory sequences, for example, by gene targeting, cosuppression, triple helix, antisense or ribozyme technology.

The present invention also relates to a method for the production of a transgenic animal, preferably mouse, comprising introduction of a recombinant DNA molecule or vector of the invention into a germ cell, an embryonic cell or an egg or a cell derived therefrom. The non-human animal to be used in the method of the invention may be a wildtype, i.e. healthy animal, or may have a disease or disorder, preferably a disease or disorder which is dependent on neovascularzation, such as solid tumors, retinopathy, arthritis, psoriasis. Said disease or disorder may be an inborn insufficiency or natural developed or caused by genetical engineering, for instance by the expression of a DNA sequence encoding a protein involved in neuronal development and/or diseases as described above, preferably under the control of the regulatory sequence of the invention.

The invention also relates to transgenic nonhuman animals comprising a recombinant DNA molecule or vector of the invention or obtained by the method described above, preferably wherein said recombinant DNA molecule is stably integrated into the genome of said non-human animal, preferably such that the presence of said recombinant DNA molecule or vector leads to the transcription and/or expression of the heterologous DNA sequence by the regulatory sequence of the invention. Further non-human animals which may be employed according to the embodiments of the invention as described above are well known to the person skilled in the art and comprise rat, hamster, dog, monkey, rabbit, pig.

With the regulatory sequences of the invention, it is now possible to study in vivo the regulation of Flk-1 expression during angiogenesis. Furthermore, since VEGF and VEGF receptor genes seem to have different functions in different stages of development, it is now possible to determine domains of said proteins which may be important for their biological activity and/or for the regulation of their activity. In addition, it is now possible to in vivo study mutations which affect different functional or regulatory aspects of VEGF or its receptor or vector of the invention.

Moreover, the present invention relates to a method for the identification of a chemical and/or biological substance capable of suppressing or activating and/or enhancing the transcription of a gene in endothelial cells comprising:

(a) contacting a cell of the invention or the transgenic non-human animal of the invention either of which is capable of expressing the heterologous DNA sequence with a plurality of compounds; and
(b) determining those compounds which suppress or activate and/or enhance the expression of said heterologous DNA sequence.

Said plurality of compounds may be comprised in, for example, samples, e.g. cell extracts from, e.g. plants, animals or microorganisms. Furthermore, said compounds may be known in the art but hitherto not known to be capable of suppressing or activating and/or enhancing the transcription of a gene in endothelial cells. The plurality of compounds may be, e.g., added to the culture medium or injected into the animals.

The term "plurality of compounds" in a method of the invention is to be understood as a plurality of substances which are either identical or not. If a sample containing a plurality of compounds is identified in the method of the invention, then it is either possible to isolate the compound from the original sample identified as containing the compound capable of suppressing or activating and/or enhancing the transcription of a gene in endothelial cells, or one can further subdivide the original sample for example, if it consists of a plurality of different compounds, so as to reduce the number of different substances per sample and repeat the method with the subdivisions of the original sample. Depending on the complexity of the samples, this can be done several times, preferably until the sample identified according to the method of the invention only comprises a limited number of or only one substance(s). Preferably said sample comprises substances of similar chemical and/or physical properties, most preferably said substances are identical.

Determining whether a compound is capable of suppressing or activating and/or enhancing the transcription of a gene in endothelial cells can be done, for example, in mice by monitoring reporter gene expression or by monitoring behavior of the transgenic non-human animals of the invention contacted with the compounds compared to that of wild-type animals or compared to a transgenic non-human animal contacted with a compound which is either known to be capable or incapable of suppressing or activating and/or enhancing the transcription of a gene in endothelial cells of said transgenic non-human animal of the invention. Furthermore, the person skilled in the art can monitor the physical behavior, or for example the movement of the above-described animals. Such methods are well known in the art. Such regulators of Flk-1 gene expression may be used in processes such as wound healing; in contrast, antagonists of expression may be used in the treatment of tumors that rely on vascularizatlon for growth. Thus, the present invention provides methods for identifying compounds which modulate VEGF receptor (e.g., Flk-1 or Flt1) gene expression. Compounds found to downregulate expression of a VEGF receptor gene can be used in methods to inhibit angiogenesis, while compounds found to enhance Flk-1 or Flt1 expression can be used in methods to promote angiogenesis, for example, to promote wound healing (e.g., healing of broken bones, bums, diabetic ulcers, and traumatic or surgical wounds) or to treat peripheral vascular disease, atherosclerosis, cerebral vascular disease, hypoxic tissue damage (e.g., retinopathy, hypoxic damage to heart tissue), diabetic pathologies such as chronic skin lesions, or coronary vascular disease. These compounds can also be used to treat patients who have, or have had, transient ischemic attacks, vascular graft surgery, balloon angioplasty, frostbite, gangrene, or poor circulation. Compounds identified as having the desired effect (i.e., enhancing or inhibiting Flk-1 expression) can be tested further in appropriate models of endothelial cell growth and angiogenesis which are known to those skilled in the art. Given the therapeutic value of the compounds identified in accordance with the above-described method the present invention also relates to a method for the production of a pharmaceutical composition comprising the steps of the method of the invention and formulating the compound identified in step (b) in a pharmaceutically acceptable form.

The therapeutic compounds identified using the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired. For example, a salve or transdermal patch that can be directly applied to the skin so that a sufficient quantity of the compound is absorbed to increase vascularization locally may be used. This method would apply most generally to wounds on the skin. Salves containing the compound can be applied topically to induce new blood vessel formation locally, thereby improving oxygenation of the area and hastening wound healing. Therapeutic doses are determined to be appropriate by one skilled in the art.

Furthermore, identification of transacting factors which interact with the regulatory sequences of the invention can form the basis for the development of novel therapeutics for modulating conditions associated with endothelial cell growth, such as angiogenesis, vascular disease, and wound healing. Identification of transacting factors is carried out using standard methods in the art (see, e.g., Sambrook, supra, and Ausubel, supra). To determine whether a protein binds to the regulatory sequences of the invention standard DNA footprinting and/or native gel-shift analyses can be carried out. In order to identify the transacting factor which binds to the regulatory sequence of the invention, the regulatory sequences can be used as an affinity reagent in standard protein purification methods, or as a probe for screening an expression library. Once the transacting factor is identified, modulation of its binding to the regulatory sequence in the Flk-1 gene can be pursued, beginning with, for example, screening for inhibitors of transacting factor binding. Enhancement of Flk-1 expression in a patient, and thus enhancement of angiogenesis, may be achieved by administration of the transacting factor, or the gene encoding it (e.g., in a vector for gene therapy). In addition, if the active form of the transacting factor is a dimer, dominant-negative mutants of the transacting factor could be made in order to inhibit its activity. Furthermore, upon identification of the transacting factor, further components in the pathway of Flk-1 signal transduction can be identified. Modulation of the activities of these components can then be pursued, in order to develop additional drugs and methods for modulating endothelial cell growth and angiogenesis.

As discussed in the background section of the description of the present invention, the interaction of VEGF and its receptor play an important role in the onset of angiogenic disease. Transgenic non-human animals expressing VEGF and/or its receptor gene and/or mutated versions thereof under the control of the regulatory sequences of the invention can now be used for the identification of substances, which, for example, are capable of restoring the wild-type interaction of mutated VEGF and its receptor either or both of which bear mutations. Some genetic changes lead to altered protein conformational states. Genetic changes may therefore result in a decreased binding activity of VEGF. Restoring the activity of mutant VEGF protein or increasing the activity of other proteins which interact with mutant VEGF proteins is the most elegant and specific means to correct these molecular defects. In addition, some genetic changes may result in altered conformational states of the receptor. This, in turn, may functionally inactivate the tyrosine kinase activity, making it incapable of signal transduction. In order to restore the function of such mutant proteins an antibody may be used which binds to an epitope and induces a conformational change of the protein thereby restoring the wild type function. Thus, the methods of the invention are also useful to screen e.g., antibody, Fab, Fv or scFv expression libraries wherein the DNA sequence encoding said antibodies or derivatives thereof are under the control of the regulatory sequence of the invention. It is, of course, evident to the person skilled in the art that also other protein or peptide expression libraries using the regulatory sequences of the invention may be employed.

Further, the present invention relates to the use of the recombinant DNA molecule, vector, cell, pharmaceutical compositions, diagnostic compositions or a transgenic non-human animal of the invention for the identification of a chemical and/or biological substance capable of suppressing or activating and/or enhancing the transcription, expression and/or activity of genes and/or its expression products in endothelial cells.

In a preferred embodiment, the chemical or biological substance used in the methods and uses of the present invention is selected from the group consisting of peptides, proteins, nucleic acids, antibodies, small organic compounds, hormones, neural transmitters, peptidomimics, and PNAs (Milner, Nature Medicine 1 (1995), 879–880; Hupp, Cell 83 (1995), 237–245; Gibbs, Cell 79 (1994), 193–198).

The present invention further relates to a method of inhibiting a vascular disease in a subject, comprising contacting an artery of said subject with the recombinant DNA molecule or vector of the invention, wherein said protein reduces or prevents the development of the vascular disease, preferably said protein reduces proliferation of smooth muscle cells.

In a further embodiment the present invention relates to the use of a recombinant DNA molecule, vector, nucleic acid molecule of the invention and/or substance identified by a method of the invention for the preparation of a composition for directing and/or preventing expression of genes specifically in endothelial cells and/or for the preparation of a pharmaceutical composition for treating, preventing and/or delaying a vascular disease and/or a tumorous disease in a subject. The upregulation and activation of the Flk-1 receptor in peri-tumoral endothelial cells is believed to be involved in the neovascularization of various human or experimental tumors (Plate, 1994; Ferrar, Curr. Opin. Nephrol. Hypertens. 5 (1996), 35–44). This hypothesis is supported by experiments in which the inhibition of Flk-1-mediated signal transduction strongly inhibits tumor angiogenesis and tumor growth (Millauer, Nature 367 (1994), 576–579; Millauer, Cancer Res. 56 (1996), 1615–1620). Thus, by using compounds of the present invention described above capable of inhibiting Flk-1 gene expression, it is possible to ameliorate tumorous diseases which depend on the expression of the FLK-1 gene.

In a further embodiment, the present invention relates to the use of a recombinant DNA molecule, vector and/or the nucleic acid molecule of the invention for the preparation of a pharmaceutical composition for inducing a vascular disease in a non-human animal or in a transgenic nonhuman animal described above.

In a preferred embodiment of the methods and uses of the invention, the vascular disease is atherosclerosis and/or a neuronal disorder. Further possible methods and uses in accordance with the present invention will be evident to the person skilled in the art and are described in, for example, WO 95/13387, WO 94/11499 and WO 97/00957.

The recombinant DNA molecules, vectors, nucleic acid molecules, compounds, uses and methods of the invention can be used for the treatment of all kinds of disorders and diseases hitherto unknown as being related to or dependent on the modulation of genes specifically expressed in the endothelium. The recombinant DNA molecules, vectors, nucleic acid molecules, compounds, methods and uses of the present invention may be desirably employed in humans, although animal treatment is also encompassed by the methods and uses described herein. Thus, the present invention provides for the use of a regulatory sequence as defined above for enhancing and/or directing gene expression in endothelial cells in any kind of organism.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352–364.

The figures show:

FIG 1: Nucleotide sequence of the murine Flk-1 gene (SEQ ID NO:1). The ATG codon is at position +299. The three exons are indicated in bold. Motifs for transcription factors are underlined. VRE: vascular response element. Enhancer elements of the present invention that confer expression in endothelial cells are found in the first intron (nucleotides 7027 to 10642). These enhancer elements include the nucleotide sequence from nucleotide 8260 to nucleotide 10560, froth nucleotide 8336 to nucleotide 10608 and/or from nucleotide 10094 to nucleotide 10608.

FIG. 2: Map of reporter gene construct pGL2-B. Arrows symbolize functional elements. Luc: luciferase gene, AMP: ampicillin resistance gene, f1ori: replication origin for bacteriophage f1.

Figure 3:
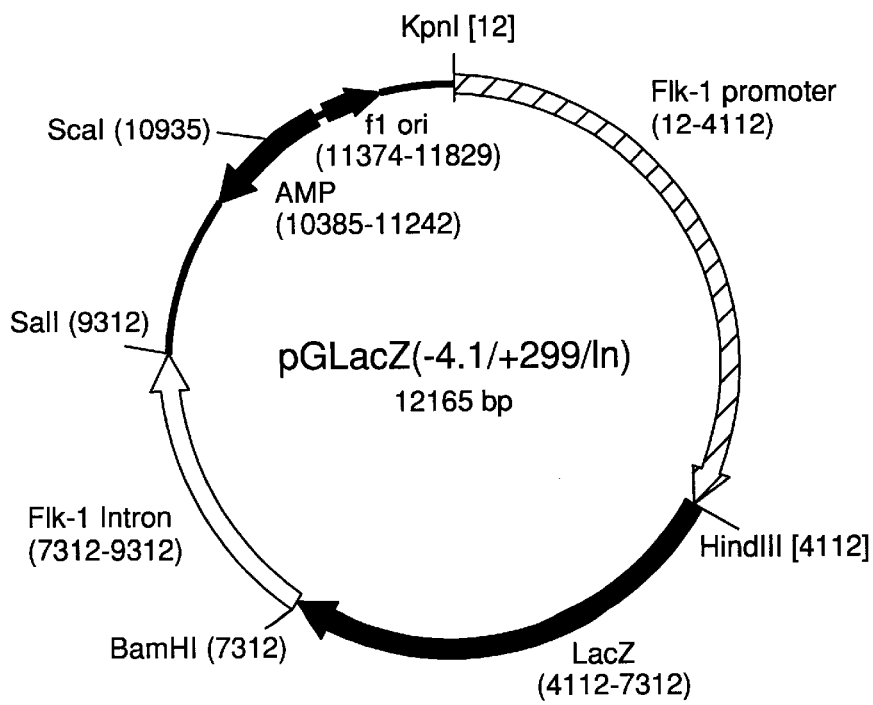

FIG. 3: Map of reporter gene construct pGLacZ. Arrows symbolize functional elements. LacZ: β-galactosidase gene, AMP: ampicillin resistance gene, f1ori: replication origin or bacteriophage f1.

FIG. 4: Partial structure and functional analysis of the mouse Flk-1 locus. A) Restriction enzyme map of the region encompassing the first three exons (represented by hatched boxes). Subfragments containing parts of intron 1 or intron 2 are indicated. Abbreviations for restriction enzymes are: B, BamHI, Xh, Xhol, Sl, SalI. B and C, luciferase reporter gene assays of various constructs following transient transfection of bovine aortic endothelial cells. B) Transfection assay of the intron fragments in combination with the Flk-1 promoter region of bp −640 to bp +299. The values were coordinated with 5'-In1 fragments with respect to the activity of the construct. C) The intron fragments were tested in combination with a 4.4 kbp Flk-1 promoter fragment spanning the region from −4.1 kbp to +299 bp of the Flk-1 gene. NIH 3T3 cells were used as a reference for non-endothelial cells. RLU, relative light units FIG. 5: Analysis of the intron in transgenic mice. The embryo (10.5 days) was stained overnight with X-Gal. The reporter gene was under the control of the intron enhancer (3'-In1, cf. FIG. 4A) and of the Flk-1 promoter fragment ranging from nucleotides −4100 to +299. A) Top lateral view. B) Top dorso-cranial view.

Figure 5:
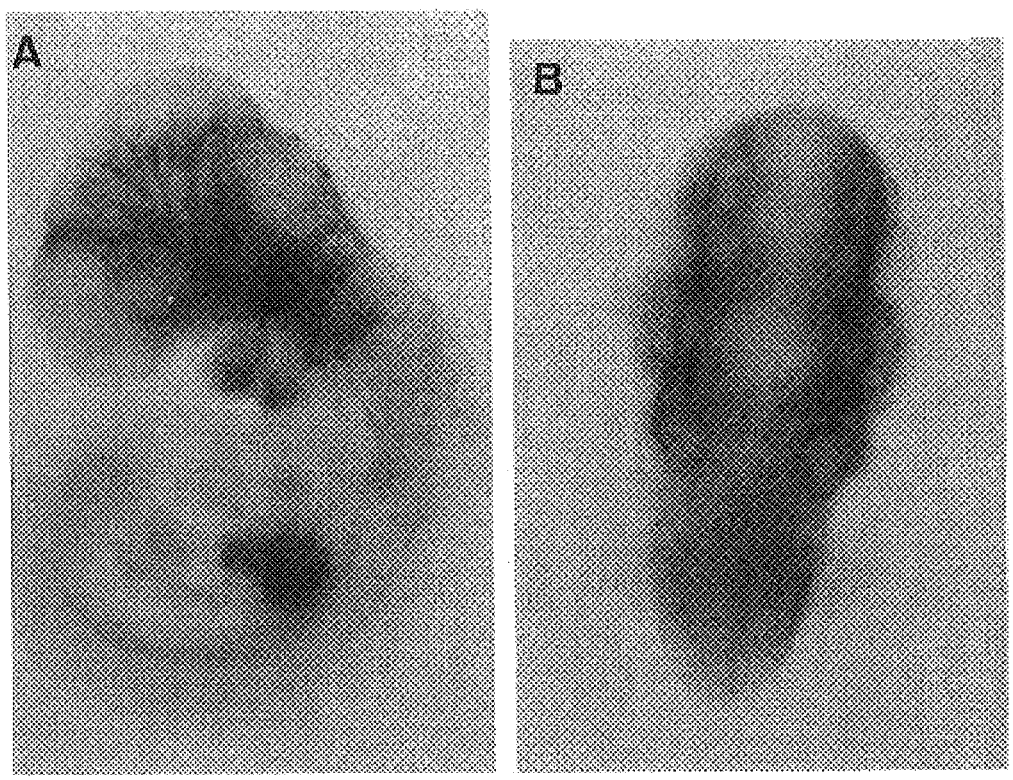
Figure 6:
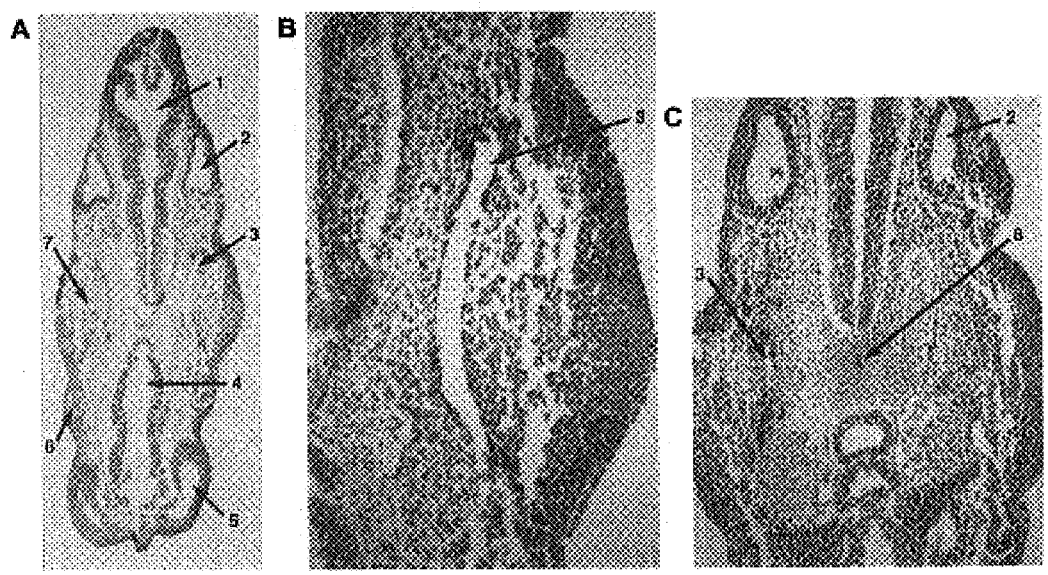

FIG. 6: Histological evaluation of a transgenic embryo. The embryo shown in FIG. 5 was embedded in paraffin. The cuts were stained with neutral red. A) Pseudo transversal cut through the head region. B) Magnification of a section from A. C) Pseudo transversal cut of a caudal region. 1: 4th ventricle of cerebrum, 2: acoustic vesicle/otocyte, 3: V. cardinalis anterior. 4: third ventricle of cerebrum. 5: endbrain vesicle. 6: optic vesicle. 7: ganglion trigeminale (V). 8: chorda dorsalis.

Figure 7:
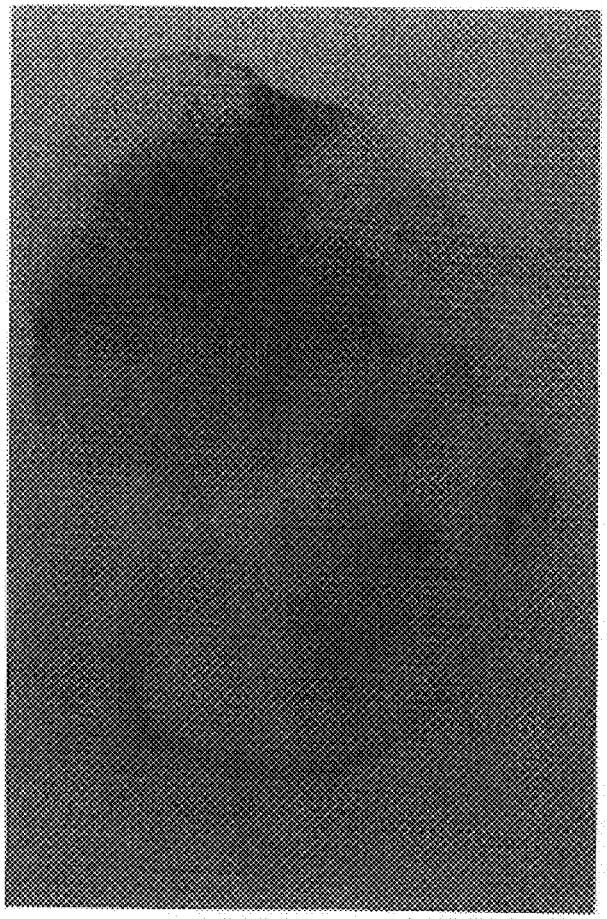

FIG. 7: Functional analysis of the first two introns of the Flk-1 gene in vivo. The depicted embryo (10.5 days) carries the β-galactosidase gene under the control of the Flk-1 promoter (−4.1 kbp to +299 bp) and the first 6.2 kbp of the transcribed region (cf. FIG. 4A). The staining was carried out as described in FIG. 5.

Figure 8:
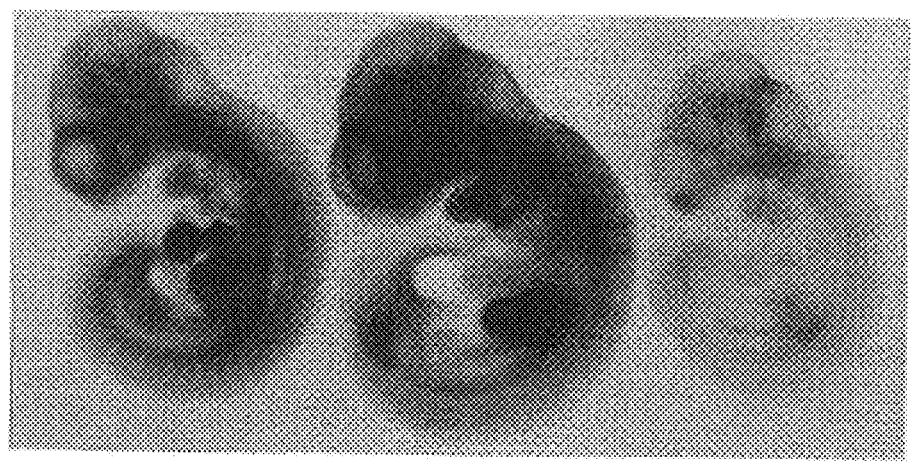

FIG. 8: In vivo characterization of the intron enhancer in combination with the strongest promoter fragment. All three embryos carry the β-galactosidase gene under the control of the Flk-1 promoter fragment of bp −640 to bp +299 and the intron enhancer. The staining was carried out as described in FIG. 5.

Figure 9:
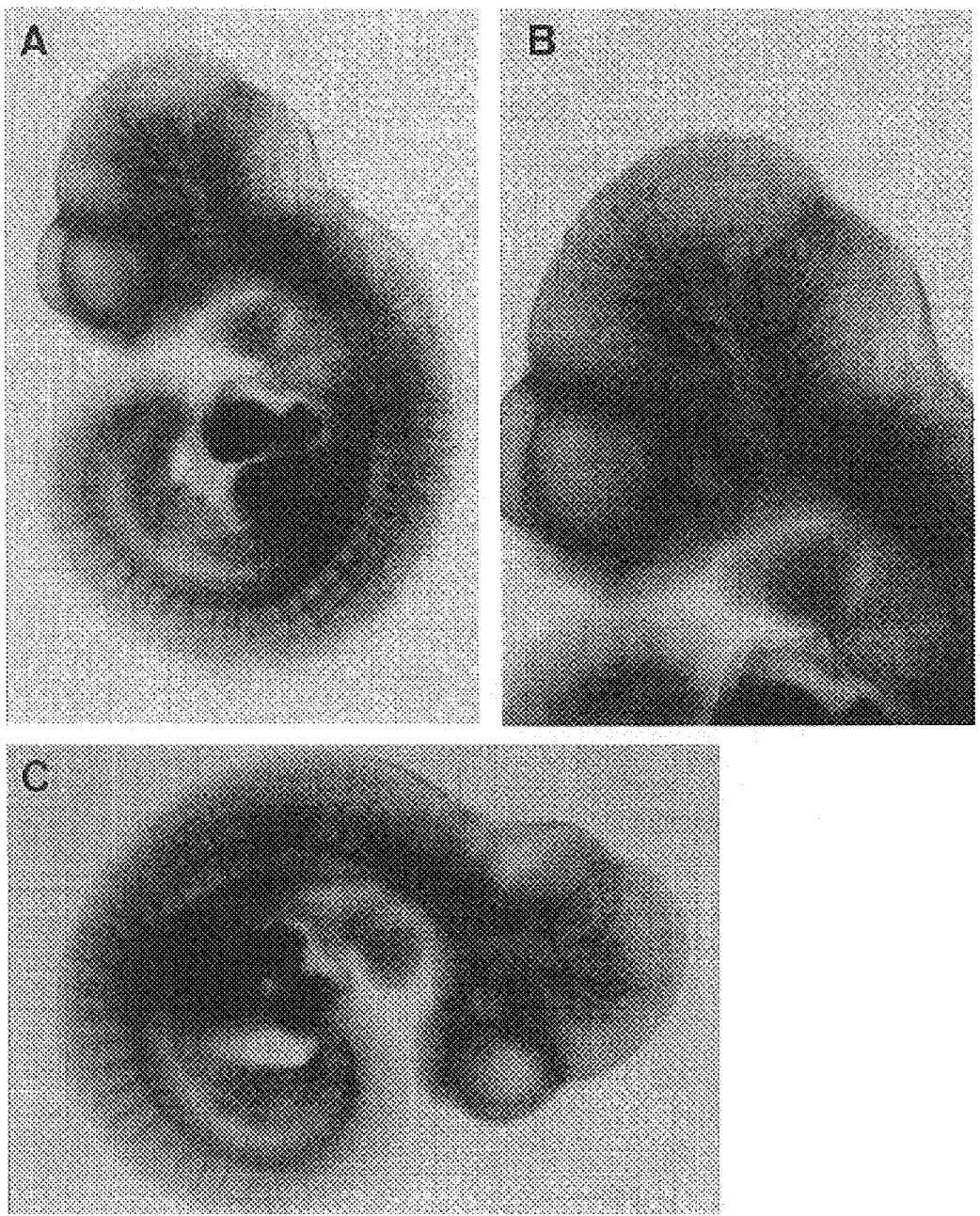

FIG. 9: Detailed analysis of the left-hand embryo from FIG. 8A) Left lateral view. B) Sectional magnification of A. C) Right lateral view.

Figure 10:
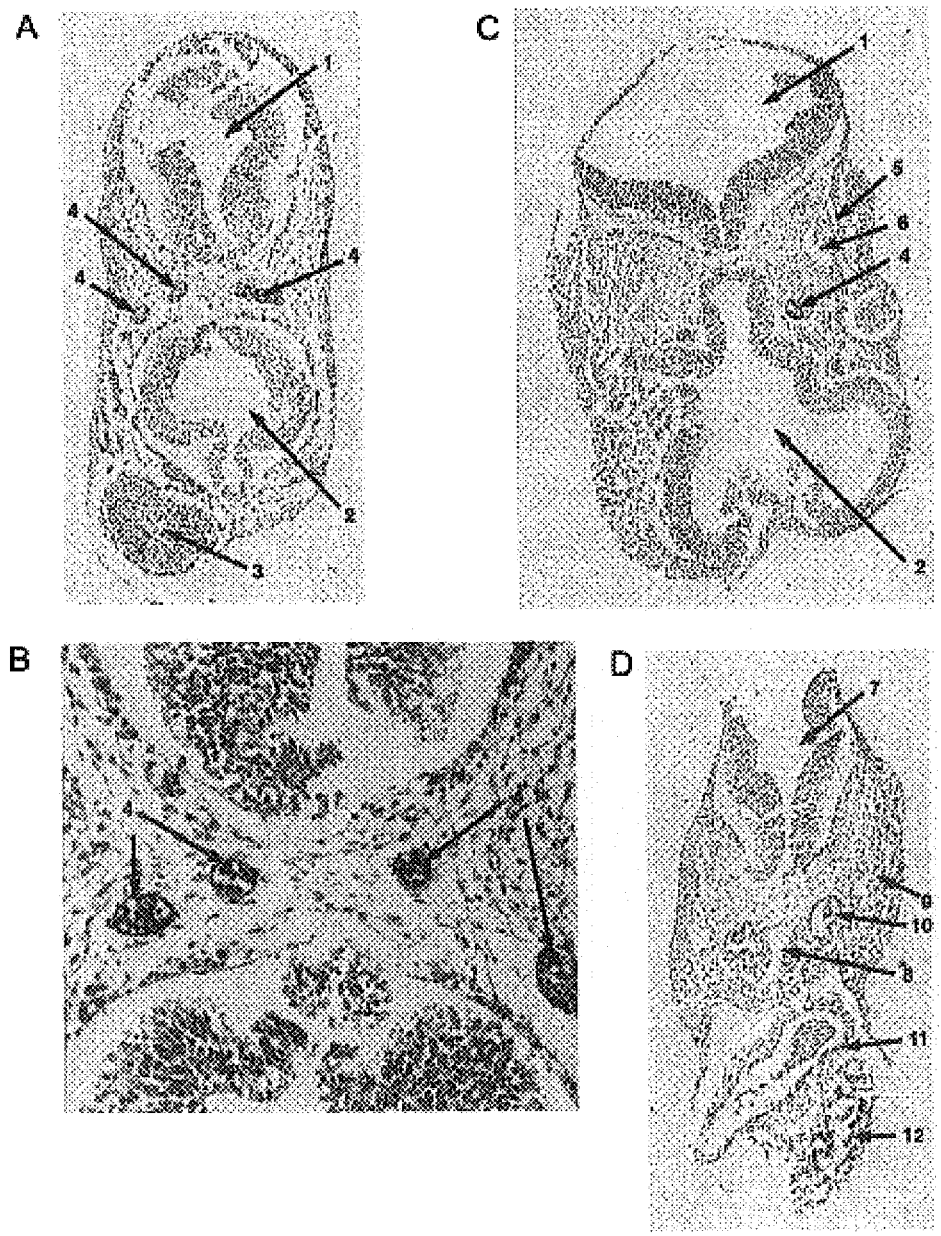

FIG. 10: Histological evaluation of the embryo depicted in FIG. 9. The embryo was embedded in paraffin and was cut into 10 μm slices. The cuts were stained with neutral red. A) Pseudo transversal cut through the head region. B) Magnification from a similar cut level as in A. C) Pseudo transversal cut from a more caudally located section. D) Pseudo transversal cut from thoracal section. 1: 4th ventricle cerebrum, 2: 3rd ventricle cerebrum, 3: endbrain vesicle, 4: A. carotis interna, 5: ganglion trigeminale (V), 6: V. cardinalis anterior, 7: neural tube, 8: esophagus, 9: V. cardinalis posterior, 10: aorta dorsalis, 11:

endocardium of the heart atrium, 12: vessels of the myocardium.

Figure 11:
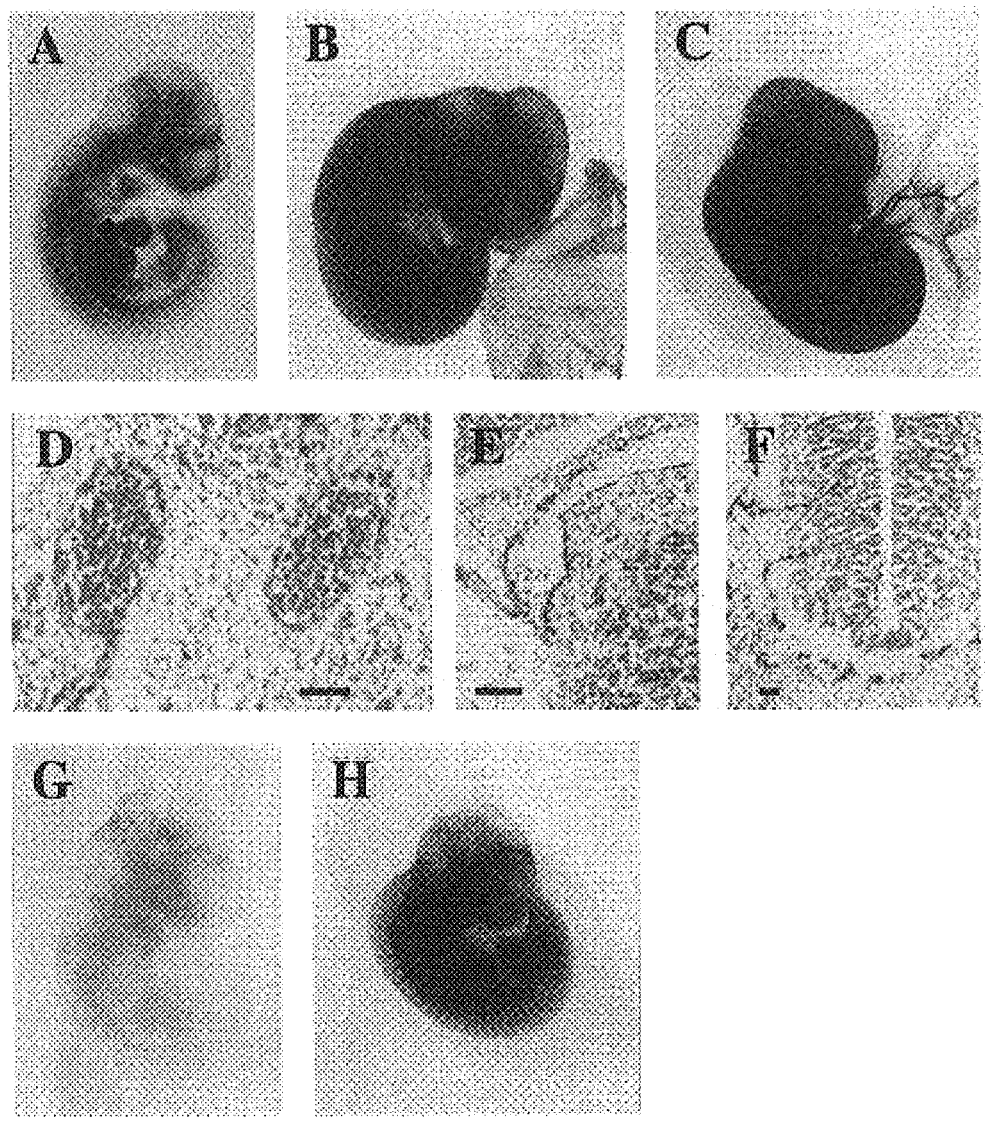

FIG. 11: Reporter gene analysis of Flk-1 gene regulatory elements in transgenic mouse embryos. The lacZ reporter gene was fused to regulatory elements derived from the mouse Flk-1 gene and tested for β-galactosidase expression in transgenic mouse embryos. A) 10.5 day transgenic mouse embryo expressing lacZ under the control of a 939 bp promoter fragment in combination with a 2.3 kbp Xhol/BamHI fragment of the first intron spanning the region from +1677 bp to +3947 bp of the Flk⁻1 gene. This embryo was derived from a foster mother. Most if not all developing vascular structures show β-galactosidase expression, for example the endocardium of the heart, the dorsal aorta, intersomitic vessels or vessels of the developing brain. B) 11.5 day embryo of a transgenic mouse line that was established with the same construct. C) An 11.5 day Flk-1/lacZ knock-in embryo in which the lacZ gene is expressed from the endogenous Flk-1 locus shows a highly similar staining. However, note the absence of β-galactosidase expression in small blood vessels of the yolk sac. D–F) Paraffin sections of the β-galactosidase stained embryo from (B) demonstrate β-galactosidase expression in the paired dorsal aortae (D), a venous vessel connected with the heart (E), and capillaries invading the neural tube (F). G) β-galactosidase expression in a transgenic embryo containing the tk promoter in combination with the 2.3 kbp Xhol/BamHI fragment of the Flk-1 first intron. H) β-galactosidase expression in a transgenic embryo containing a construct with Flk-1 promoter sequences (−640 bp/+299 bp) in combination with the 510 bp SwaI/BamHI fragment of the first intron spanning the region from +3437 bp to +3947 bp of the Flk-1 gene. Bar D)–F) 100 μM.

FIG. 12: Nucleotide sequence of the Flk-1 intron enhancer and putative transcription factor binding sites. Sequences matching known transcription factor binding sites are underlined. This sequence is deposit in the GeneBank database (accession number AF061804).

Figure 13:
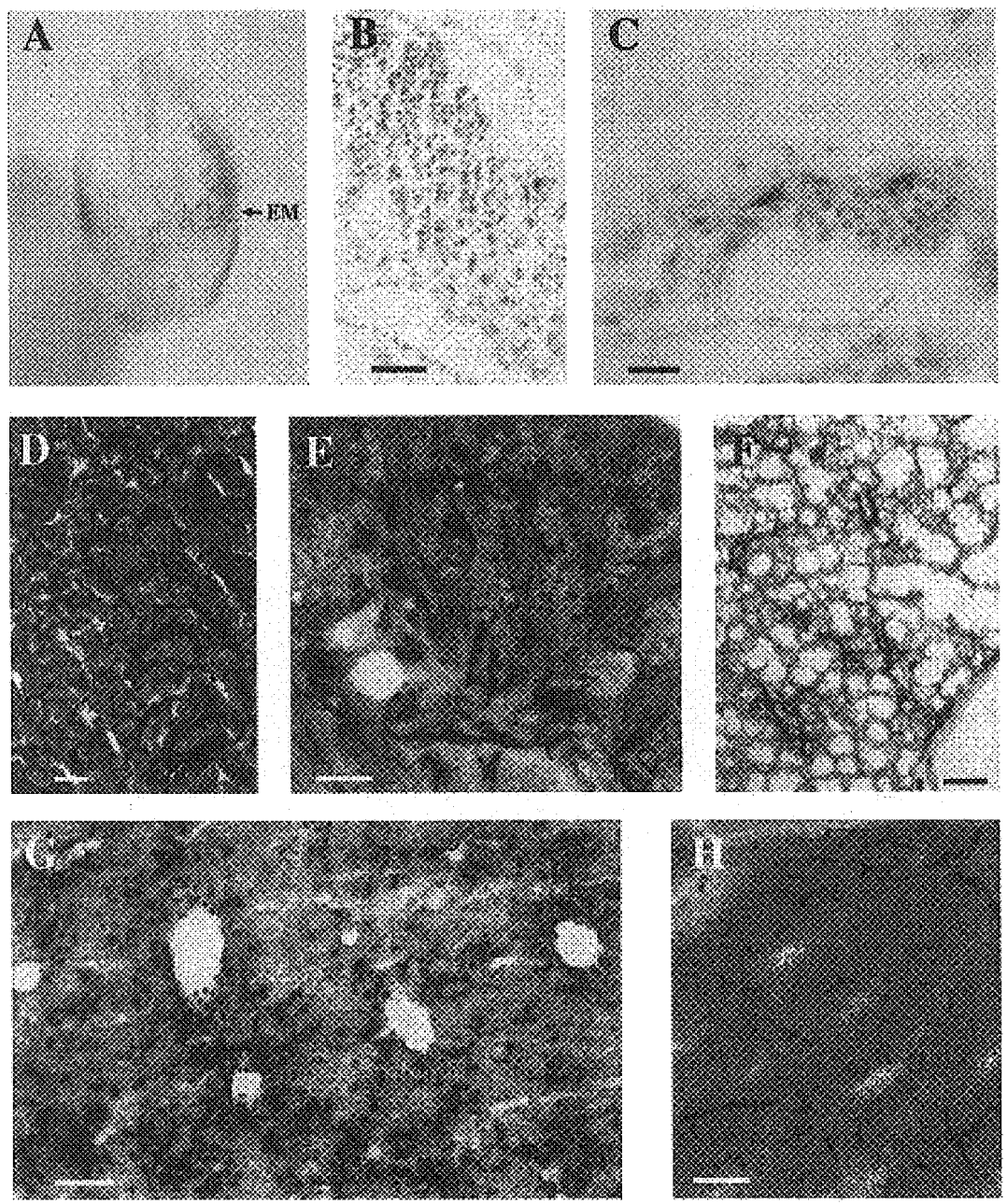

FIG. 13: Analysis of transgene expression during early development and in newborn mice. The transgenic mouse line 2603 expresses lacZ under the control of the Flk-1 promoter (−640 bp/+299 bp) in combination with the 2.3 kbp Flk-1 intronenhancer A) Frontal view on a whole mount β-galactosidase stained 7.8 day embryo. The arrow indicates transgene expression in the extraembryonic mesoderm. B) and C) Paraffin sections from the embryo shown in A demonstrate transgene expression in endothelial cells of the allantois (B) and the yolk sac (C). D–H, LacZ staining of spleen (D), kidney (E), lung (F), liver (G) and thymus (H) from a postnatal day 5 transgenic mouse. EM, extraembryonic mesoderm. Bars, 25 μM (C), 100 μM (B,D,E,F,G,H).

Figure 14:
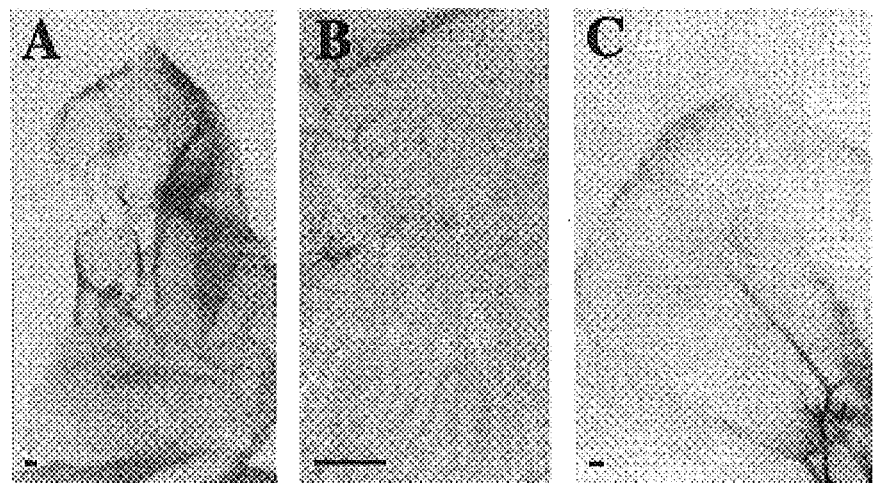

FIG. 14: The 5'-UTR is required for expression of the Flk-1 gene in the yolk sac vasculature. Transgenic mouse embryos that contain a Flk-1 promoter and 5'UTR (−640 bp/+299 bp)/enhancer (+1677 bp/+3947 bp) reporter gene construct show a complete vascular expression in the yolk sac vasculature (A and B). In contrast, the yolk sac of Flk-1/lacZ knock-in embryos which lack part of the 5'UTR show expression only in large collecting vessels that connect with the embryo, but not in the smaller vessels (C). Bar, 500 μM.

Figure 15:
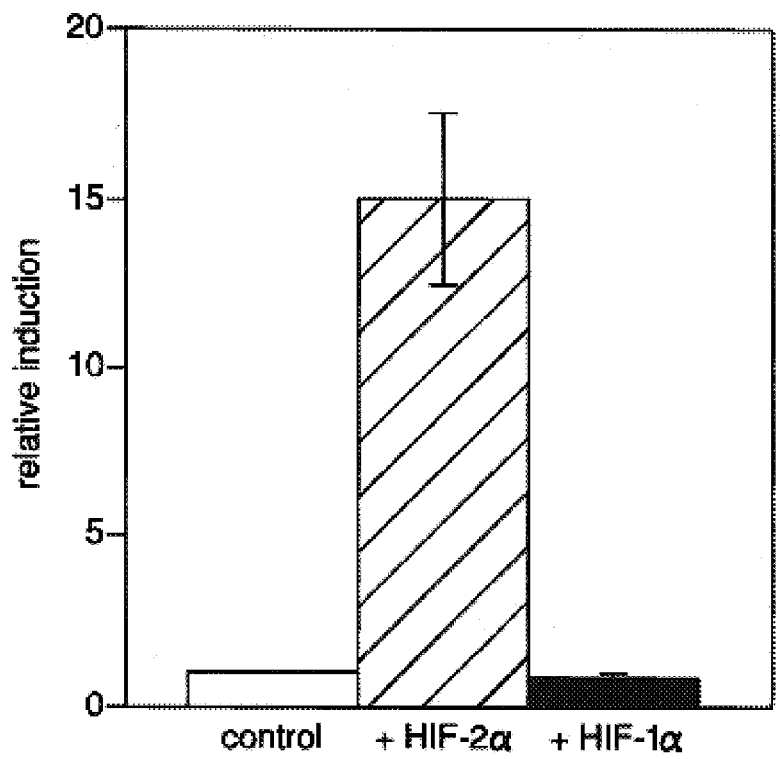

FIG. 15: HIF-2α stimulates Flk-1 gene expression. A293 cells were co-transfected with a reporter gene construct containing Flk-1 promoter sequences from bp −640 to bp +299 and with expression vectors encoding the murine HIF-1α and HIF-2α cDNAs, respectively. Relative promoter activities were determined as described in Materials and Methods. The promoter activity of the control transfection was arbitrarily set to 1.

The examples illustrate the invention.

Example 1

Cloning and Construction of Flk-1 Intron/Reporter Gene Vectors

DNA clones containing the 5' region of the mouse Flk-1 gene were isolated from a library prepared from 129/SvJ mice in λ Dash II vector (Stratagene) (Rönicke, supra) or in λ FIX II or obtained from the P1 Library (Genome Systems, St. Louis). A 21 kb region of the mouse Flk-1 gene, contained in the DNA insertions of two λ phages 6 and 16, including approximately 15 kb of 5' flanking sequences, exons 1, 2 and 3, and introns 1 and 2 was characterized by restriction enzyme mapping and Southern blot analysis. Lower DNA fragments of the phage clones were cloned into pBluescript vector DNA (Stratagene) and used for further characterization. Sequencing was performed using an automatic Sequencer (373A, Applied Biosystems). The nucleotide sequence of the Flk-1 intron enhancer is deposited in the Genbank database (accession number AF061804). The search for potential transcription factor binding sites was performed with the MatInspector software (Quandt, (1995) Nucl. Acids Res. 23, 4878–4884).

The DNA sequence (SEQ ID NO: 1) of a 12.8 kb region spanning from about position −6,660 kb (relative to the transcriptional start site) to approximately position +6,135 kb (located in the third exon) was determined (FIG. 1). FIG. 4A shows a schematic representation of the first 6.5 kbp of the transcribed region of the murine Flk-1 gene. Exons I, II and III are emphasized as hatched boxes. The first intron having a length of 3.6 kbp is subdivided into two regions (5'-In1 and 3'-In1). The region In-2 contains the entire second intron, the second exon, the 3' end of the first intron and part of the third exon. This subdivision into various intron fragments was maintained in the following analyses. The reporter gene constructs used were derived from pGL2 basic vector (Promega) that contains a promoteriess luciferase gene. Luciferase reporter gene constructs were generated for transfection of cells in vitro. For use in transgenic mice in vivo, plasmids were used in which the luciferase reporter gene was replaced by a lacZ reporter gene.

In order to generate (luciferase) reporter gene constructs, Flk-1 promoter fragments were amplified by PCR and cloned into pGL2 (Promega) vector DNA 5' to the luciferase gene as described by Rönicke, supra; see also FIG. 2. In short, the upstream primers used were −1900: 5'-GGG GTA CCG AAT TCT AAA TGG GGC GAT TAC C-3' (SEQ ID NO 2); −640: 5'-GTG GTA CCC AM CAC TCA ACA CCA CTG-3' (SEQ ID NO: 3); −624, 5'-TCG GTA CCG ACC CAG CCA GGA AGT TC-3' (SEQ ID NO: 4); the downstream primer was +299, 5'-TTG CTA AGC TTC CTG CAC CTC GCG CTG GG-3' (SEQ ID NO: 5). To generate the construct ranging from −4100 to +299, a HindIII-EcoRI fragment of recombinant lambda phage 6 from P1 Library (Genome Systems, St Louis) was inserted into the plasmid ranging from −1900 to +299. Vectors that contained Flk-1 intron sequences in addition to promoter sequences were generated as follows: specific intron sequences were amplified by PCR from cloned Flk-1 genomic DNA and inserted downstream of the reporter gene. Primers used for amplification were 5'-In1down: 5'-AGG GAT CCA CTC TTT AGT AGT AAG GCG-3' (nucleotides 7036–7057 of SEQ ID NO: 1, SEQ ID NO: 6); 5'-In1up: 5'-ACC TCG AGA CTT GGA TGG CAC-3' (nucleotides 8324–8342 of SEQ ID NO: 1, SEQ ID NO: 7); 3'-In1down: 5'-GGG CTA TAA TTG GTG CCA TCC-3' (nucleotides 8312–8332 of SEQ ID NO: 1, SEQ ID NO: 8); 3'-In1up: 5'-GGA TGG AGA AAA TCG CCA GGC-3' (nucleotides 10637–10658 of SEQ: ID NO: 1, SEQ ID NO: 9); IN2A: 5'-GTG TGC ATT GTT TAT GGA AGG G3' (nucleotides 10571–10593 of SEQ ID NO: 1, SEQ ID NO: 10); IN2B: 5'-CAT AGA CAT AAA CAG TGG AGG C-3' (nucleotides 12849–12871 which is part of the cDNA sequence published by Millauer (1993), supra, SEO ID NO: 11). For the subsequent experiments the vector indicated in FIG. 3 was used. It represents a modification of the pGL2 basic vector in which the corresponding Flk-1 promoter fragments were inserted into the KpnI and HindIII restriction sites of the polylinker (FIG. 2). Also the luciferase reporter gene was replaced by the β-galactosidase gene (Schlaeger, Proc. Natl. Acad. Sci. USA 94 (1997), 3058–3063). For an analysis of the intron intron fragments were cloned into the BamHI and SalI restriction sites indicated. DNA manipulations, PCR amplification and DNA sequencing were performed according to conventional methods known in the art as described, for example in Sambrook, supra and PCR Technology, Griffin and Griffin, eds., RC Press London (1994).

Example 2

Functional Analysis of the Intron of the Flk-1, Gene In Vitro

FIG. 4 shows the result of transient transfections in BAECs. The corresponding intron fragments were combined with a Flk-1 promoter fragments which comprised nucleotides −640 to +299. The promoter activity was standardized with respect to the promoter activity of the construct containing the 5'-In1 fragment.

Tissue culture and transient transfections were performed as follows:

All cells were cultured in DMEM+supplemented with 10% FCS (Sigma) and as described in Schaeger, 1997. bEnd5 cells were generated by transformation with the Polyoma middle-T oncogene as described earlier (Montesano, Cell 62 (1990), 435–445). Bovine aortic endothelial cells (BAECs) were prepared as described (Schwartz, In vitro 14 (1978), 966–980). NIH 3T3, C2C12 and L cells were obtained from ATCC. Transient transfections were performed using the CaPO$_4$-precipitation method according to Chen and Okayama (Mol. Cell Biol. 7 (1987), 2745–2752), optionally with modifications as described (Rönicke, 1996). The transfection efficiency was monitored by co-transfection of a β-galactosidase reporter vector.

Each construct was transfected at least six times in three independent experiments. Cells were grown to 70% confluence in 6-cm dishes prior to transfection. Cells were washed 16 hrs after addition of CaPO-precipitate and incubated for further 48 hrs. In each experiment, 6 µg luciferase and 1 µg pCMV5 (Rönicke, supra) lacZ reporter gene constructs were used. Cells were lysed in 1×reporter-lysis-buffer (Promega) for 15 min on a test tube-rotator. After centrifugation, the supernatant was transferred to a fresh tube and stored at −80° C. or taken for luciferase-and lacZ-assay immediately. Reporter-gene assays for β-galactosidase activity were performed according to Eustice (Biotechniques 11 (1991), 739–740). Chlorophenol red-β-D-galactopyranoside (CPRG) was used as a substrate and the conversion was measured at 575 nm in an ELISA-reader (Biometra). Extracts were diluted to obtain OD$_{575}$ nm values between 0.2 and 0.8. These values were used to standardize for transfection efficiency after subtracting a background value, as determined from a cell extract of a transfection without lacz-reporter plasmid but with a luciferase-reporter plasmid. Luciferase-reporter gene assays were performed with the same extracts as described by the manufacturer (Promega). Luciferase activity was measured with a luminometer (LB96P, Berthold) and calculated as per cent of the activity of the pGL2-promoter plasmid (Promega).

TABLE I

Functional analysis of the intron of the Flk-1 gene. The upper line indicates the corresponding intron fragment which was analyzed in combination with the Flk-1 promoter (−640 bp/+299 bp).

| Construct | 5'-In1 | 3'-In1 | In2 |
| --- | --- | --- | --- |
| BAEC | 100 +/− 0% | 128 +/− 34% | 136 +/− 52% |
| 3T3 | 100 +/− 0% | 55 +/− 15% | 74 +/− 33% |

Figure 4C:
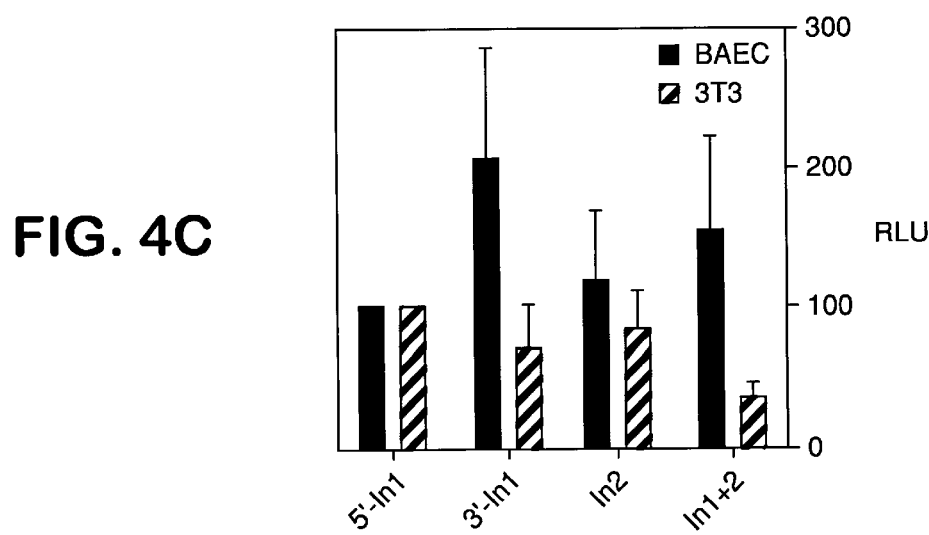

FIG. 4C shows the results of another transfection assay of the intron fragments. It was carried out as described above, with the exception that a Flk-1 promoter fragments was used that comprised the region between nucleotides −4100 and +299. Also, a fragment was analyzed that contained the entire first intron, the second exon, the second intron and part of the third exon shown in FIG. 4A.

TABLE II

Functional analysis of introns of the Flk-1 gene. The upper line indicates the corresponding intron fragment which was analyzed in combination with the Flk-1 promoter (−4100 Bp/+299 Bp).

| Construct | 5'-In1 | 3'-In1 | In2 | In1 + 2 |
|---|---|---|---|---|
| BAEC | 100 +/− 0% | 206 +/− 81% | 119 +/− 51% | 154 +/− 68% |
| 3T3 | 100 +/− 0% | 71 +/− 32% | 85 +/− 27% | 35 +/− 12% |

An analysis of this experiment revealed that the construct with the 3' region of the first Intron in BAECs had an activity that was twice that of that containing the 5' region of the first intron. Also, it showed 85% higher activity than the construct with the second Intron (p=0.0153). The 4.5 kbp longer construct In1+2 that also contained the 3' region of the first intron, too, revealed an activity that was markedly higher in BAECs than in 3T3 cells.

A functional analysis of the first 6.5 kbp of the transcribed region of the murine Flk-1 genes lead to the identification of an endothelial-specific positive regulatory element. This regulatory sequence is located in the region between the XhoI and BamHI restriction site in the first intron of the Flk-1 gene (cf. FIG. 4A). It is functional in both orientations since the intron is used in an antiparallel manner with respect to the Flk-1 promoter fragment in the construct referred to as 3'-In 1. In construct In1+2, however, the original orientation was maintained. A sequence analysis of the intron enhancer lead to the identification of two potential GATA binding sites at position +1927 bp and +3514 bp; (Evans, Proc. Natl. Acad. Sci. USA 85 (1988), 5976–5980; Orkin, Blood 80 (1992), 575–581), a potential AP-1 binding site at position +2210 bp; (Lee, Cell 49 (1987), 741–752) and two PEA3 consensus sequences at position +3494 bp and +3741 bp; (Martin, Proc. Natl. Acad. Sci. USA 85 (1988), 5839–5843).

Example 3

Functional Characterization of the Flk-1 Promoter In Vivo

So far, analyses of the murine Flk-1 promoter have been restricted to in vitro systems (Rönicke, supra; Patterson, supra). The investigation of the promoter activity in vitro is an important tool in promoter characterizing since it is useful to assay a large number of promoter constructs for their activity in a short time. However, this situation is always an artificial one since not all factors that are relevant in vivo can also be reconstituted in vitro. While an in vitro investigation of a promoter yields important information on the mechanisms of gene regulation it is only the in vivo characterization that can yield the final proof for the relevance of the elements identified. An excellent test system for promoter analysis in vivo are transgenic mice. In this model the corresponding promoter fragment was cloned before a reporter gene, isolated together with this reporter gene and injected into fertilized mouse oocytes. In many cases, successful integration of the promoter reporter construct into the mouse genome lead to transgenic mice which contain the construct in every cell. This test system, in addition to the analysis of the promoter activity during embryonic development and in the adult animal, allows a tissue-specific characterization of the promoter activity.

For the investigation of the Flk-1 promoter in transgenic mice the bacterial β-galactosidase reporter gene was chosen since the gene product is easily detectable by color reaction and remains at the location of production due to its limited solubility. In this manner it is possible to identify cells in which the corresponding Flk-1 promoter fragment since only there an expression of β-galactosidase took place. When producing transgenic mice it was taken care that no regions originating from the vector were injected along with the promoter. First, Flk-1 promoter fragments comprising the regions between nucleotides −640 and +299, −1900 and +299 as well as −4100 and +299 were investigated. The constructs were based on plasmid pGL-2B described in FIG. 2 with the exception that the luciferase reporter gene was replaced by the β-galactosidase gene. All injection fragments used in the examples were obtained by restriction digestion with the enzymes KpnI and SalI. Transgenic mice were generated as described by (Hogan, Manipulating the Mouse Embryo (1994), Cold Spring Harbor Laboratory Press, New York). Fertilized oocytes were isolated from superovulated C57BL/6×C3H/He F1 mice, microinjected and reimplanted into pseudopregnant females of the same hybrid-mouse strain. Mice were sacrifized at day 10.5 or 11.5 of gestation, and embryos were analyzed by whole mount LacZ staining for transgene expression. The embryos to be examined were isolated on day 10 after reimplantation of the injected oocytes. Analysis of the transgenic embryos revealed that although promoter activity could be detected, none of the constructs was capable of conferring reproducible expression of the reporter gene in the endothelium.

Example 4

Functional Characterization of the Flk-1 Intron In Vivo

After analysis of the Flk-1 promoter region from −4.1 kbp to +299 Bp the intron which was identified in vitro was then examined for its function in vivo. For this purpose, a construct similar to that shown in FIG. 3 was used which contained an Flk-1 promoter fragment ranging from nucleotide −4100 to base pair +299 and the intron enhancer (3'-In1, cf. FIG. 4A). The staining and fixation of the embryos was performed as follows: The mid-day of the plug observation was counted as E0.5. The embryos were dissected out in ice-cold PBS and fixed in ice-cold 2% (w/v) paraformaledehyd, 2 mM $MgCl_2$, 2 mM EGTA, 0.1 M Pipes buffer, pH 6.9 for 15 to 120 minutes. The embryos were rinsed with PBS three times for 5 minutes each. The LacZ expression was detected by incubating the embryos at 30° C. overnight in 0.1% X-gal (5-bromo4-chloro-3-indolyl-β-D-galactopyranoside), 5 mM potassium ferricyanide, 5 mM potassium ferrocyanide 5 mM, 1 to 2 mM magnesium chloride, 0.002 to 0.02% NP-40. 0.01% or 0.25 mM sodium deoxycholate, PBS, pH 7.0. After the staining, embryos were rinsed in PBS and postfixed at 4° C. overnight in 2% paraformaldehyde, 0.1% glutaraldehyde, PBS, pH 7.0. For whole-mount photography, the postfixed embryos were rinsed in PBS and equilibrated for 3 minutes each in (optionally 30%) 50% glycerol and then in 70% glycerol. FIG. 5 shows an embryo (embryonic day 10.5) which was isolated after injection of the fragment. In FIG. 5A a color reaction in vessels of the developing brain can be clearly discerned. Also superficial vessels in the body's middle (dorsal) and a staining in the liver bud can be observed. FIG. 5B shows the dorsal, caudal region of the same embryo. It proves that the vessels in both halves of the head were stained.

For an exact localization of the stained cells the embryo was embedded in paraffin, cut into slices of 10 μm and counterstained with neutral red. Cryostat sectioning and lacZ staining of organs from postnatal mice was performed as described (Schlaeger, 1997).

The results of the histological analysis are shown in FIG. 6. It shows pseudo transversal cuts of the embryo. In section 6A a staining of the inner lining of the V. cardinalis anterior (3) and of other superficial vessels can be seen. FIG. 6B represents a strong magnification of a section of 6A with the staining of endothelial cells within the V. cardinalis anterior. FIG. 6C shows a more caudally located region. Again, the staining of the V. cardinalis anterior and of superficial vessels with wide lumen and thin walls as well as of vascular structures in the neural tube is clearly visible. Also, a staining of the chorda dorsalis (9) can be observed. However, in none of the cases a staining of arterial vessels could be observed.

The subsequent injection of the same fragment lead to a total of eight further transgenic embryos which displayed an identical expression pattern albeit in two cases of weaker nature. Thus, the intron enhancer exhibited in vivo an effect that was even more marked than in vitro. In combination with a promoter fragment which on its own had a very variable expression pattern it ensures a reproducible expression pattern with clear endothelium specificity, however, covering a substantial part of the endogenous Flk-1 expression pattern.

Example 5

Functional Analysis of the Introns I and II of the Murine Flk-1 Gene In Vivo

Since the intron enhancer in combination with an Flk-1 promoter fragment displayed an endothelium-specific function in transgenic mice covering a substantial part of the endogenous expression pattern, the further search for in vivo relevant, gene regulatory elements was extended to other intron regions. For this purpose, the construct containing the promoter region between nucleotides −4100 to +299 and the first 6.5 kbp of the transcribed region (In1+2; cf. FIG. 4) was used. FIG. 7 shows an embryo on embryonic day 10.5 which was obtained after injection of this fragment. Again, a staining of the vessels in the developing brain as well as superficial vessels the of the liver bud was visible. The following injections yielded four further transgenic embryos which displayed the same pattern. A combination of the promoter region used with only the 5' end of the first intron (5'-In1; cf. FIG. 4), however, yielded no endothelium-specific expression pattern.

Example 6

Combination of the Intron Enhancer with the Flk-1 Promoter Fragment that was the Most Potent In Vitro To investigate whether the repressing elements of the murine Flk-1 promoter between nucleotides −4100 and −640 are functional also in combination with the intron enhancer, a shorter construct without these inhibitory regions was used for further analysis. It contain the intron enhancer (3'-In1) and the 5' region from base pair −640 to nucleotide +299. This 5' region displayed the highest activity in vitro. FIG. 8 shows three transgenic embryos (embryonic day 10.5) which were obtained after injection of the fragment. All three display a more marked staining in vascular structures than the embryos analyzed so far. While the embryo on the right hand shows a weak staining, the left-hand embryo yields a very strong expression in virtually all vessels. The embryo in the middle holds a medium position as regards the completeness of its expression pattern, i.e., it lacks expression in the heart although it resembles strongly the embryo on the left hand as regards the staining of the other structures. In FIG. 9A the left-hand embryo from FIG. 8 is shown in more detail. The strong staining of the heart in the region of the atrium and ventricle is particularly clearly visible. Furthermore, the vessels of the developing brain, the vessels between the somites, the aorta dorsalis as well as the fine capillary plexus on the body's surface are stained. FIG. 9B shows a sectional magnification of 9A. Here, the staining of the vessels in the head region as well as the expression in the superficial capillary plexus is visible. In FIG. 9C the same embryo is shown from the other side. In addition to the structures described in FIG. 9A also a staining of the chorda dorsalis can be observed.

The embryo shown in FIG. 9 was embedded in paraffin and cut to slices. The cuts dyed with neutral red are shown in FIG. 10. FIG. 10A shows a pseudo transversal cut through the head region. Particularly prominent is the branching of the A. carotis interna (4) In addition to the staining of other vascular structures. FIG 10B represents a magnification of a similar cut; here, too, the branching of the A. carotis interna is particularly striking. FIG. 10C shows a more caudal cut which in terms of its position roughly corresponds to the cut shown in FIG. 6A. Here, however, in addition to the staining of the V. cardinalis anterior (6) an expression in the branching of the A. carotis interna (4) and other vascular structures is visible. FIG. 10D represents an even more caudally located region. A staining in the venous endothelium (V. cardinalis posterior, 9) and in the arterial structures (aorta dorsalis, 10) can be observed. Furthermore, the endocardium of the atrium as well as the vessels in the trabeculae of the heart ventricles display an expression.

A total of seven transgenic embryos was analyzed after injection of this fragment (−640 bp/+299 bp/3'-In1). Safe for one which showed no staining, all embryos displayed an expression of the β-galactosidase in endothelial structures. The staining was regularly more marked than in combination with the negative regulatory elements between nucleotides −4100 and −640. Thus, the in vitro identified regions displayed a function in vivo. The deletion of these negative regulatory elements yielded a construct that lead to a reproducible expression in venous and arterial endothelium.

Example 7

Endothelium-specific Expression Mediated by Flk-1 Regulatory Sequences In Vivo

When the Flk-1 promoter fragment with the strongest in vitro activity (−640 bp/+299 bp; Rönicke, supra) was tested in combination with the 2.3 kbp XhoI/BamHI fragment of the first intron that showed endothelium-specific activity in vitro (3'-In1; +1677 bp/+3947 bp; see Example 6), a reproducible vascular lacZ expression in transgenic E10.5 mouse embryos derived from foster mothers was observed (Table III). In these embryos, the lacZ reporter gene was expressed in developing vascular structures, such as capillaries in the head region, intersomitic vessels, the dorsal aorta, and in the heart anlage (FIG. 11A). Sectioning of these embryos confirmed that the β-galactosidase protein was confined to vascular endothelium. This in vivo analysis demonstrated that the intron sequences in combination with the Flk-1 promoter confer an endothelium-specific expression pattern that closely resembles the expression pattern of the endogenous Flk-1 gene (Millauer, 1993). Moreover, the intron fragment could also direct endothelial cell-specific lacZ expression when used in an inverted orientation in the reporter construct (Construct −640 bp/+299 bp//+3947 bp/+1677 bp; see Table III).

TABLE III

Summary of the in vivo activity of different flk-1 constructs

| Construct | TG | ES | ET | NO |
| --- | --- | --- | --- | --- |
| −4100/+299 | 11 | 0 | 3 | 8 |
| −1900/+299 | 31 | 1 | 10 | 20 |
| −640/+299 | 3 | 0 | 1 | 2 |
| −640/+299 // 3'Intron +1677/+3947 | 7 | 6 | 0 | 1 |
| −640/+299 // 3'Intron +3947/+1677 | 4 | 3 | 1 | 0 |
| −640/+299 // 3'Intron +3437/+3947 | 7 | 5 | 0 | 2 |
| −640/+254 // 3'Intron +1677/+3947 | 12 | 8 | 1 | 3 |
| tk // 3'intron +1677/+3947 | 15 | 3 | 0 | 12 |
| −5500/+299 // Intron I + II | 3 | 2 | 0 | 1 |

Embryos transgenic for the constructs given above were generated, and LacZ staining and genotyping was performed at E10.5 or E11.5 as described in Example 4. Constructs are defined by the position of the promoter or intron fragments in bp relative to the transcription initiation site of the endogenous Flk-1 gene. TG, number of transgenic embryos; ES, number of embryos showing endothelial-specific staining; ET, number of embryos showing ectopic staining; NO, number of embryos showing no staining at all.

Transgenic mouse lines were generated with this reporter gene construct (−640 bp/+299 bp//+1677 bp/+3947 bp) containing the Flk-1 regulatory sequences. One of these lines (2603) showed a complete vascular expression of the reporter gene at E11.5 and was analyzed further (FIG. 11B). Sectioning of β-galactosidase stained E11.5 transgenic embryos revealed that reporter gene expression was confined to the endothelium of blood vessels, e.g. in the endothelium of the dorsal aorta (FIG. 11D), in venous vessels (FIG. 11E) and in the perineural vascular plexus and sprouting capillaries invading the neural tube (FIG. 11F). To determine whether transgene expression in this mouse line reproduced the complete expression pattern of the endogenous Flk-1 gene, the lace staining pattern of these embryos was compared to heterozygous Flk-1 mutant mouse embryos which express the lacZ gene from the endogenous Flk-1 locus (Shalaby, Nature 376 (1995), 62–66). In these knock-in mice, the lacZ gene was inserted into the endogenous Flk-1 locus via homologous recombination and is therefore expected to reproduce the expression pattern of the endogenous Flk-1 gene (Shalaby, 1995). The lacZ staining pattern of transgenic embryos and the knock-in embryos at E11.5 was indistinguishable (FIGS. 11B,C). It is concluded from these data that the −640 bp/+299 bp promoter region of the Flk-1 gene and the 2.3 kbp Xhol/BamHI fragment of the first intron contain regulatory elements that are sufficient for endothelial-specific gene expression in developing mouse embryos.

Example 8

The First Intron of the Flk-1 Gene Contains an Autonomous Endothelium-specific Enhancer To assess the role of the 2.3 kbp Xhol/BamHI fragment of the first Flk-1 intron in endothelium-specific gene expression, it was further investigated whether the intron sequences can confer endothelium-specific expression to the heterologous herpes simplex virus-thymidine kinase (tk) promoter. This promoter has no intrinsic endothelial cell specificity (Schlaeger, 1997). A lacZ reporter gene construct was generated that contained the tk promoter, in combination with the 2.3 kbp BamHI/Xhol fragment of the first intron (+1677 bp/+3947 bp). The tk promoter sequences were amplified from the plasmid ptkSDKlacZ (Schlaeger, 1997) using oligonucleotides tk5' (5'-CCGGTACCCAAACCCCGCCCAGCGTCTTG3'; SEQ ID NO: 16) and tk3' (5'-CCGACAAGCTTGGTCGCTCGGTGTTCGAGG-3'; SEQ ID NO: 17). The PCR product was digested with Kpnl and HindIII.

From the β-galactosidase reporter construct described in Example 2 (FIG. 2), Flk-1 promoter sequences were exised and removed by Kpnl and HindIII digestion. The tk promoter was then subcloned in the Kpnl and HindIII restriction sites of the vector. Transgenic mouse embryos generated with this construct showed vascular reporter gene expression (FIG. 11G). The β-galactosidase staining observed in these embryos was weaker than in embryos expressing lacZ under the control of the −640 bp/+299 bp Flk-1 promoter in combination with the intron fragment (FIGS. 11A,B). Also, the frequency of transgenic mouse embryos expressing this transgene was significantly reduced, when compared with constructs driven by the −640 bp/+299 bp Flk-1 promoter in combination with the intron fragment (Table III). This indicates that the tk promoter lacks positive acting elements which are present within the Flk-1 promoter. However, these results show that the Flk-1 intron fragment alone, in contrast to the Flk-1 promoter, can reproducibly target reporter gene expression to the endothelium. Taken together, the results of both the in vitro an in vivo experiments in this study demonstrate that sequences located in the first intron of the mouse Flk-1 gene act as an autonomous endothelium-specific enhancer.

In order to further characterize the minimal intron sequences that are required for endothelium-specific expression, we analyzed whether shorter intron fragments were also active in combination with the 939 bp promoter region of the Flk-1 gene (−640 bp/+299 bp). By this deletion analysis, the intron enhancer was localized to a 510 bp Swal/BamHI fragment (+3437 bp/+3947 bp) which is located immediately upstream of the second exon. This fragment was sufficient to stimulate endothelium-specific lacZ expression in transgenic mouse embryos (FIG. 11H, Table III. The DNA sequence of this fragment (FIG. 12) contains potential binding sites for the GATA and Ets transcription factors, and for Scl/Tal1, all of which have been implicated to play a role in angiogenesis (reviewed by Risau, Nature 386 (1997), 671–674). Whether these consensus sequences represent functional transcription factor binding sites remains to be determined.

Example 9

Flk-1 Regulatory Sequences Target Endothelium-specific Transgene Expression Throughout Development To test whether the regulatory sequences of the Flk-1 promoter and enhancer identified can reproduce the endogenous Flk-1 expression pattern throughout development, the lacZ expression pattern of the transgenic mouse line 2603 (FIG. 11B) was further analyzed at various stages of embryonic development and at postnatal days 5 (P5) and 120 (P120). In this mouse line, the transcription of lacZ is driven in combination by the −640 bp/+299 bp Flk-1 promoter and the 2.3 kbp BamHI/Xhol intron enhancer fragment. The earliest stage during which transgene expression was detectable by whole mount LacZ staining was in E7.8 embryos (FIG. 13A). This is the earliest stage that was examined. The analysis of sections of these embryos confirmed that the transgene was expressed in angioblasts of the allantois and the yolk sac (FIGS. 13B,C). Moreover, transgene expression was restricted to the vascular endothelium at all stages of embryonic development examined. To determine if the transgene expression persists after birth, we performed lacZ staining of cryostat sections from several different organs of P5 and P120 transgenic mice. Strong LacZ staining was detected in vessels of the spleen, kidney, thymus, liver and lung from P5 animals (FIGS. 13D–H). However, lacZ expression was downregulated in most vascular beds of P120 animals, as is the case for the endogenous Flk-1 (Millauer, 1993; Kremer, Cancer Res. 57 (1997), 3852–3859). Taken together, these results support the conclusion that the identified Flk-1 regulatory sequences (the 939 bp promoter in combination with the intron enhancer) are sufficient to reproduce most, if not all properties of the endogenous Flk-1 expression.

Example 10

The 5'-UTR of the Flk-1 Gene is Required for Expression of Flk-1 in the Yolk Sac Vasculature In Flk-1/lacZ knock-in embryos, the lacZ gene is under control of all endogenous regulatory elements except for the regions from bp +137 to bp +299 in the 5'-UTR and approximately the first 600 bp of the first intron (Shalaby, 1995). It has been shown in accordance with the present invention that the intron sequences deleted in the knock-in construct created by Shalaby (1995) are not required to generate the strong and complete endothelial-specific reporter gene expression which is mediated by the Flk-1 regulatory sequences described in this study (FIG. 11B and Table III). However, since the complete Flk-1 5'-UTR is present in the reporter gene construct which directs the most complete vascular-specific lacZ expression (–640 bp/+299 bp//+1677 bp/+3947 bp; FIG. 11B and Table III), it allows to study the consequences of a partial 5'-UTR deletion on Flk-1 expression in vivo: Genomic DNA was prepared from unstained embryos or yolk sacs. Genotyping was performed by PCR analysis using the primer pairs –258 fw/LacRev or LacZP1/LacZP2. Primers for PCR analysis were: –258 fw: 5'-ATGGTACCCAGGTTGCTGGGGGCAG-3' (SEQ ID NO: 12); LacRev: 5'-TGGTGCCGGAAACCAGGCAAA-3' (SEQ ID NO: 13); LacZP1: 5'-ATCCTCTGCATGGTCAGGTC-3' (SEQ ID NO: 14); LacZP2: 5'-CGTGGCCTGATTCATTCC-3' (SEQ ID NO: 15). The complete vascular staining of the Flk-1/lacZ knock-in embryos at E11.5 indicates that the 5'-UTR is not essential for vascular expression in the embryo proper. However, the yolk sac staining pattern of Flk-1/lacZ knock-in embryos and of transgenic mice from this study that harbored constructs containing the complete 5'-UTR were markedly different (FIGS. 14A–C). The uniform vascular lacZ expression in the transgenic yolk sacs from this study (FIGS. 14A, B) was absent in small vessels of the yolk sacs of the knock-in embryos (FIG. 14C), in which only large yolk sac vessels were stained. In addition, it was found that replacement of the entire Flk-1 promoter including the 5'-UTR by the tk promoter in the present transgenic construct (Table III) leads to a similar lacZ expression pattern in the yolk sacs as that described in the yolk sacs of the Flk-1/lacZ knock-in embryos. Thus, the 5'-UTR might be involved in specifying Flk-1 expression in a subset of endothelial cells.

Example 11

The Role of HIF-2α in Flk-1 Regulation

The Flk-1 promoter (–640 bp/+299 bp) confers endothelium-specific expression to the firefly luciferase reporter gene in transfected bovine aortic endothelial cells (Rönicke, 1996) and provides for a strong reporter gene transcription in vivo; see Examples 6 to 10. This suggests that transcription factors that are specifically expressed in endothelial cells activate the Flk-1 promoter in a cell-type specific manner.

The basic helix-loop-helix PAS-domain transcription factor, HIF-2α (also known as HLF, HRF or EPAS1), is expressed in endothelial cells during mouse embryonic development (Ema, Proc. Natl. Acad. Sci. USA 94, 4273–4278, 1997; Flamme, Mech. Dev. 63 (1997), 51–60; Tian, Genes Dev. 11 (1997). 72–82) and is thus a candidate to regulate Flk-1 expression. HIF-2α has previously been shown to stimulate both the expression of VEGF (Ema, 1997) and Tie2 (Tian, 1997). To determine if HIF-2α might be involved in the regulation of Flk-1 gene expression, A293 cells were co-transfected with a luciferase reporter gene construct containing Flk-1 promoter sequences (–640 bp to +299 bp) and an eukaryotic expression vector that contained the mouse HIF-2α cDNA. Mouse HIF-2α and HIF-1α cDNAs were obtained from a mouse brain capillary endothelial cell cDNA library (Schnürch, Development 119 (1993), 957–968) with a 300 bp BamHI/NcoI fragment spanning the 5'UTR of HIF-1α. Positive phages were rescreened, and inserts were amplified by PCR using oligonucleotides HIF Start: (5'-GGGAATTCACCATG AGTTCTGAACGTCGAAAAG-3'; SEQ ID NO: 18) and HIF Flag Stop: (5'-AAGCGGCCGCTCATTTATCGTCATCGTC-CTTGTAATCGTTAACTTGATCCAAAG CTCTG-3'; SEQ ID NO: 19). The PCR product was digested with Eco RI and NotI and subcloned in the EcoRI and NotI restriction sites of pcDNA3 expression vector. The murine HIF-2α cDNA was obtained as described (Flamme, 1997). The phage insert was amplified by PCR using oligonucleotides HRF START (5'-GGGAATTCACCACAATGACAGCTGACAAGGAG'; SEQ ID NO: 20) HRF rev (5'-AAGCGGCCGCTCATTTATCGTCATCGTC-CTTGTAATCGTTGGTGGCCTGGTCCA GAGCTCTGAG-3'; SEQ ID NO: 21) and PCR product was digested with EcoRI/NotI and cloned into the EcoRI and NotI sites of pcDNA3. The sequence encoding the FLAG epitope was included in the reverse oligonucleotide primer. HIF-2α and HIF-1α expression plasmids were constructed by inserting the FLAG-tagged cDNAs into the EcoRI and NotI sites of pcDNA3 (Invitrogen). For co-transfection assays, A293 cells were split 1:2 into 35 mm dishes and transfected 18 hours later with 4 µg of DNA (2 µg of Flk-1 promoter-driven luciferase plasmid, 1 µg of CMV promoter-driven β-galactosidase expression plasmid, and 1 µg of the HIF-2α or HIF-1α expression plasmids, or pBluescript SKII and pcDNA3 as a control) using a transfection kit (MBS, Stratagene). After 20 hours, reporter gene activity measurements were performed using the Dual Light Kit (Tropix, Bedford, Mass.). The luciferase activity of each extract was normalized to the respective β-galactosidase activity. Endogenous background levels of both enzyme activities were measured using extracts from mock-transfected cells and were subtracted. The normalized luciferase activity of the control transfection was arbitrarily set to 1. Each value represents the average of at least six experiments.

In comparison to cells transfected with the luciferase reporter construct alone, co-transfection of the HIF-2α construct increased reporter gene activity approximately 15-fold (FIG. 15). In contrast, HIF-1α, a close relative of HIF-2 which stimulates the hypoxia-induced transcription of the VEGF gene, failed to stimulate the reporter construct (FIG.

15). These results suggest that HIF-2α regulates the expression of the Flk-1 gene.

SUMMARY

The mouse Flk-1 receptor is crucial for the differentiation of the hemangioblastic lineage and during embryonic vascular development (Risau, Annu. Rev. Cell Dev. Biol. 11 (1995), 73–91; Shalaby, 1995; Risau, 1997). Moreover, Flk-1 plays a central role in the regulation of neovascularization in a wide variety of tumors (Plate, Brain Pathol. 4 (1994), 207–218; Ferrara, 1996). To elucidate the basis of its endothelial expression, regulatory sequences of the murine Flk-1 gene have been isolated and characterized that confer endothelium-specific reporter gene expression in transgenic mouse embryos. Transgene expression driven by these sequences was strong, specific, and highly reproducible. Most importantly, it has been demonstrated that the isolated sequences were active in early stage vascular development and may thus represent a clue towards the identification of the molecular mechanisms involved in hemangioblast differentiation and vasculogenesis. Moreover, transgene expression persists until shortly after birth and is downregulated in adult animals, as it was described for the endogenous Flk-1 gene (Millauer, 1993; Kremer, 1997). Endothelium-specific expression in almost all transgenic mouse embryos tested was mediated by a 939 bp fragment of the promoter region in combination with a fragment of the first intron. 5'-flanking fragments up to –5.5 kbp alone were not sufficient to confer a reproducible endothelium-specific transgene expression. Reproducible endothelium-specific expression was therefore dependent on sequences from the first intron. These sequences also activated the heterologous tk promoter specifically in endothelial cells in vivo, and were active in an orientation independent manner. Thus, they fulfill the criteria for an autonomous tissue specific enhancer.

As demonstrated in Example 8, the intron sequences that were sufficient for endothelium-specific expression were contained in a 510 bp fragment. Several potential binding sites for known transcription factors could be identified therein (see FIG. 12), including consensus binding sites for c-ets1, PEA3 (an Ets-like transcription factor), GATA transcription factors, and Scl/Tal-1. The c-ets1 transcription factor was proposed to be involved in the early differentiation of endothelial cells from their precursors (Pardanaut, Cell Adhesion and Communication 1 (1993), 151–160). In addition, c-ets1 is expressed in endothelial cells during tumor vascularization and other forms of angiogenesis in humans (Wemert, Am. J. Pathol. 140 (1992), 119–127). Proteins of the Ets family can activate transcription through a PEA3 motif (Wemert, 1992). Transcription factors of the GATA family are involved in the transcription of genes that are expressed in the hematopoietic and endothelial lineages, such as von Willebrand factor (Jahroudi, Mol. Cell. Biol. 14 (1994), 999–1008). Unlike the hematopoietic-transcription factor GATA-1, GATA-2 is expressed in both the endothelial and hematopoiefic lineages (Elefanty, Blood 90 (1997), 1435–1447). Scl/Tal-1 has recently been implicated in the regulation of Flk-1 expression in Zebrafish (Liao, Genes Dev. 12 (1998), 621–626). The presence of two potential Scl/Tal-1 binding sites in the murine Flk-1 intron enhancer suggests that Scl/Tal-1 might regulate Flk-1 expression in mice. However, no direct effect of Scl/Tal-1 on Flk-1 expression has been observed so far in mice although Scl-null mice have vascular defects (Visvader, Genes Dev. 12 (1998), 473–479).

Recently, analyses of the regulatory elements of other endothelium-specific genes such as von Willebrand factor (Aird, Proc. Natl. Acad Sci USA. 92 (1995), 4567–4571), c-ets-1 (Jorcyk, Cell. Mol. Biol (Noisy-le-grand) 43 (1997), 211–225) or the endothelial receptors, Tie1 (Korhonen, Blood 86 (1995), 1828–1835) and Tie2 (Schlaeger, Development. 121 (1995), 1089–1098; Schlaeger, 1997) have been reported. The most uniform expression pattern reported was conferred by regulatory elements of the Tie2 gene. However, in contrast to Flk-1, expression of Tie2 and of reporter genes driven by Tie2 regulatory sequences is not downregulated in adult animals. Such as in the Flk-1 gene, the first introns of the Tie2 gene and of the Ets-1 gene are involved in endothelium-specific expression. Similar to the Flk-1 intron enhancer, the first intron of the Tie2 gene also contains an autonomous endothelial specific enhancer. A major difference between the structural organisation of the regulatory elements of the Flk-1 gene and the Tie2 gene is, however, that the Tie2 promoter by itself is active in certain embryonic blood vessels (Schlaeger, 1995). At least during the developmental stages analyzed (i.e. E10.5 and E11.5) an autonomous function of the Flk-1 promoter was not observed. The intronic 303 bp Tie2 core enhancer also contains potential binding sites for transcription factors of the Ets and GATA families (Schlaeger, 1997), and c-ets1 or PEA3 binding sites are present in the promoters of Tie1, Tie2 and Flt-1 (Korhonen, 1995; Schlaeger, 1995; Wakiya, J. Biol. Chem. 271 (1996), 30823–30828).

Analysis of Flk-1/lacZ knock-in mouse embryos that express the lacZ gene from the endogenous Flk-1 locus has previously shown that the lacZ reporter gene is expressed ubiquitously in the developing intra-embryonic vasculature and the yolk sac of E7.5 embryos (Shalaby, 1995). However, in accordance with the present invention it was found that a fragment of the 5' UTR that is deleted in the knock-in construct is required for reporter gene expression in the yolk sac vasculature during later stages of embryonic development. Based upon transient transfection analyses in bovine aortic endothelial cells, the Flk-1 5'-UTR has been shown to contain a positive acting, endothelial cell-specific element between nucleotides +136 and +299 (Rönicke, 1996). The complete vascular staining of the Flk-1/lacZ knock-in embryo proper at E11.5 demonstrates that the 5'-UTR is not essential for intraembryonic vascular expression at this developmental stage.

The involvement of HIF-2α in the regulation of Flk-1 expression further emphasizes the role of basic helix-loop-helix/PAS-domain transcription factors in the regulation of components of the VEGF signal transduction system and of vascular development. The upregulation of VEGF in response to hypoxia is generally thought to be mediated by HIF-1. Moreover, mouse embryos lacking functional genes for HIF-1α or ARNT show defects in vascular development, perhaps due to reduced VEGF levels (Maltepe, Nature 386 (1997), 403–407; Iyer, Genes Dev. 12 (1998), 149–162). This observation indicates that the physiological relevance of these transcription factors is not restricted to adaptation to hypoxia, but extends to the regulation of normal vascular development HIF-2α is expressed in various tissues, including the developing endothelium of several organs, for example in the brain (Flamme, 1997). It seems therefore likely that HIF-2α is involved in the regulation of Flk-1 expression in blood vessels that co-express HIF-2α and Flk-1. Interestingly, HIF-2α is also expressed in tissues that express the Flk-1 receptor ligand, VEGGF, and has been shown to stimulate VEGF expression (Ema, 1997). Taken together, these observations support the hypothesis that HIF-2α is both an intrinsic and extrinsic regulator of blood vessel growth and function (Flamme, 1997), by stimulating both receptor and ligand expression. The expression of VEGF and Flk-1 shows a remarkable coordinate temporal pattern both in development and in tumors. For example, VEGF and Flk-1 are expressed transiently in the developing mouse brain, and are largely down-regulated in the adult, but reactivated in brain tumors (Plate, 1994). In hemangioblastomas of the brain, which are highly vascularized tumors, both the VEGF and Flk-1 expression are highly up-regulated, and this correlates with the up-regulation of HIF-2α expression in the stromal cells of this tumor type. Whether HIF-2α contributes to the remarkably coordinated expression of VEGF and Flk-1 in other tumor types, remains to be established, since for example in glioblastomas—another cerebral tumor—up-regulation of VEGF is due to hypoxia, and HIF-2α is inducible by hypoxia. Unlike the expression of VEGF and Flt-1, Flk-1 expression is not directly stimulated by hypoxia (Gerber, J. Biol. Chem. 272 (1997), 23659–23; Kremer, 1997). Thus, the primary function of HIF-2 in the regulation of Flk-1 expression does not appear to be related to the hypoxia response.

Among the endothelial RTK identified thus far, Flk-1 is the only receptor whose function is required for the determination of the endothelial lineage. Therefore, the Flk-1 gene represents the ideal candidate for studying the transcriptional regulatory mechanisms that are active during the emergence of the endothelial lineage. The observation that the isolated regulatory elements of the Flk-1 gene are active in early stage vascular development are of great importance for this objective. Knowledge of the Flk-1 gene regulatory sequences is also of great potential relevance in the therapy of certain diseases. The Flk-1 receptor has been demonstrated to be a key regulator of angiogenesis in various diseases, including cancer (Plate, 1994). Therefore, the study of the regulatory elements involved in the upregulation of Flk-1 expression in the tumor endothelium appears to be particularly relevant for studying the mechanisms of tumor angiogenesis. Further studies will unravel whether the same regulatory elements of the Flk-1 gene that confer endothelium-specific expression in mouse embryos are also active in the tumor vasculature. Flk-1 gene regulatory elements active in the tumor vasculature may provide information about the signaling pathways that can be targeted for anti-angiogenic tumor therapy. Finally, the Flk-1 gene regulatory elements will be useful for targeting expression of genes to the vasculature. An attractive possibility is the expression of suicide genes (Ozaki, Hum. Gene Ther. 7 (1996), 1483–1490) under the control of these elements. The use of the Flk-1 gene regulatory elements in combination with, e.g., the Cre/loxP system may provide a powerful tool for specifically inactivating genes in the developing vasculature or In tumor endothelium.

The present invention is not to be limited in scope by its specific embodiments described which are intended as single illustrations of individual aspects of the invention and any DNA molecules, or vectors which are functionally equivalent are within the scope of the invention. Indeed, various modifications of the invention in addition to those shown and described therein will become apparent to those skilled in the art from the foregoing description and accompanying drawings. Said modifications intended to fall within the scope of the appended claims.

What is claimed is:

1. A recombinant DNA molecule comprising:
   (a) at least one first regulatory sequence which confers expression in endothelial cells in vivo, wherein said first regulatory sequence is selected from the group consisting of
      (i) a DNA sequence comprising a nucleotide sequence as given in SEQ ID NO: 1;
      (ii) a DNA sequence comprising a nucleotide sequence of SEQ ID NO: 1 from nucleotide 8260 to nucleotide 10560, from nucleotide 8336 to nucleotide 10608 and/or from nucleotide 10094 to nucleotide 10608; and
      (iii) a DNA sequence comprising a fragment of a nucleotide sequence of SEO ID NO: 1, wherein the fragment confers endothelial cell-specific expression; and
   (b) operatively linked thereto a heterologous DNA sequence.

2. The recombinant DNA molecule of claim 1, wherein said first regulatory sequence comprises a GATA-binding site, an AP-1 binding site, an SP1 binding site, an NFκB binding site, a STAT binding site, a ScI/tal-1 binding site, an Ets-1 binding site, a PEA3 consensus sequence or any combination(s) thereof.

3. The recombinant DNA molecule of claim 1 or 2, wherein the first regulatory sequence is a DNA sequence comprising a fragment of a nucleotide sequence from nucleotide 8260 to nucleotide 10560 of SEQ ID NO:1, from nucleotide 8336 to nucleotide 10608 of SEQ ID NO: 1, and/or from nucleotide 10094 to nucleotide 10608 of SEQ ID NO: 1, wherein the fragment confers endothelial cell-specific expression.

4. The recombinant DNA molecule of any one of claims 1 to 2, wherein said heterologous DNA sequence is operatively linked to further regulatory sequences.

5. The recombinant DNA molecule of claim 4, wherein said further regulatory sequence is a promoter.

6. The recombinant DNA molecule of claim 4, wherein said further regulatory sequence is a 3'-untranslated region.

7. The recombinant DNA molecule of claim 5, wherein said promoter is a promoter of a hypoxia inducible gene, a gene encoding a growth factor or its receptor or a glycolytic enzyme.

8. The recombinant DNA molecule of claim 7, wherein said growth factor is VEGF, PDGF or Fibroblast growth factor.

9. The recombinant DNA molecule of claim 5, wherein said promoter comprises a DNA sequence selected from the group consisting of
   (a) a DNA sequence comprising the nucleotide sequence as given in SEQ ID NO: 1 from nucleotide 6036 to nucleotide 6959;
   (b) a DNA sequence comprising the nucleotide sequence of the human Flk-1/KDR promoter; and
   (c) a DNA sequence comprising a fragment of a nucleotide sequence of any one of nucleotide 6036 to nucleotide 6959 of SEQ ID NO: 1 or the nucleotide sequence of the human Flk-1/KDR promoter, wherein the fragment confers endothelial cell-specific expression.

10. The recombinant DNA molecule of any one of claims 1 to 2, wherein at least one of said DNA sequences is of human or murine origin.

11. The recombinant DNA molecule of any one of claims 1 to 2, wherein said heterologous DNA sequence being operatively linked to said regulatory sequences is located 5' to said first regulatory sequence.

12. The recombinant DNA molecule of any one of claims 1 to 2, wherein said heterologous DNA sequence encodes a peptide, protein, sense RNA, or ribozyme.

13. The recombinant DNA molecule of claim 12, wherein said protein is selected from the group consisting of Vascular Endothelial Growth Factor (VEGF), Hypoxia Inducible Factors (HIF), HIF-Related Factor (HRF), tissue plasminogen activator, p21 cell cycle inhibitor, nitric oxide synthase, interferon-γ, atrial natriuretic polypeptide, monocyte chemotactic proteins, luciferase, green fluorescent protein and lacZ.

14. A vector comprising a recombinant DNA molecule of any one of claims 1 to 2.

15. The vector of claim 14, which is an expression vector and/or a targeting vector.

16. The vector of claim 14, further comprising a gene capable of expressing HIF-2α.

17. An isolated cell transformed with a DNA molecule of any one of claims 1 to 2.

18. The isolated cell of claim 17, which is a prokaryotic or eukaryotic cell.

19. The isolated cell of claim 17, which is an endothelial cell.

20. The isolated cell of claim 17, further comprising a recombinant DNA molecule or vector containing a gene capable of expressing HIF-2α.

21. The recombinant DNA molecule of claim 1, wherein the first regulatory sequence confers endothelium-specific expression in vivo of the heterologous DNA sequence.

22. An isolated cell transformed with the vector of claim 14.

* * * * *

SEQUENCE LISTING

```
<160> NUMBER OF SEQ ID NOS: 22

<210> SEQ ID NO 1
<211> LENGTH: 12845
<212> TYPE: DNA
<213> ORGANISM: Murine
<220> FEATURE:
<221> NAME/KEY: misc_feature
<222> LOCATION: (1)..(12845)
<223> OTHER INFORMATION: n is any nucleotide

<400> SEQUENCE: 1
tctagaatat agaagataag tttgcgtaca attcagtcct ttgaagacct gataagcttt      60
aagaaggaag atgggttaca cattgggaaa tggttgcaat ctgcacatgg cagaggcaag     120
agatgcaaat cacatttctt acatactcca tacaaatctt acaagactgt ttttctttct     180
catttaaaat aagaagacct gccagtcttc cccttattac taattacagt cactctgtat     240
ctttgttgac attggatagt tttacatact tcaacaggct ggtgtcatta aagttgtggt     300
gggtgggcac cagagacacg tgattcagag tgggaggaga tgcaggagaa acgaggcaca     360
gcagaagcag aagcgaggaa aaacactctc aacgttacta acacatcgag aggttccgca     420
cactagcaat acgggctgaa tctgacctaa tctctgctgt tgaaaatttt gcctagccgc     480
acactagcaa tacgggctga atctgaccta atctctgctg ttgaaaattt tgcctagcct     540
gtcacacaag tgctgagcat acagaaaaag gagagtaatt ctctggttct ttgactaacc     600
aaatagtcta tatcaaattg cctaagataa tgtatacatt tagtacatga ctggtttatac     660 ctattctata tgactattat ttaaatgtga atttacaagt gagcatatga agtccatttt     720
```

-continued

```
acatggctag tacatataac ttttaaaaag ttggacatag ttatatttt ccatttattt      780
atttacttta tatcctgatc acagaccccc cctcctctg gattaactct ctccactgct      840
tcttacccct cccatctct ccttcacctc tgagaagggg ggatacctcc tgtcttatct      900
ggtttcagtg ggagaaggat gtatcctaac acatataatt tttaatatcc tgagtttttc    960
tttcatacac cttacttatt ctattcattt ttcaggaagg catgtttaat gtttttttt     1020
taattttatg tgtacgagtg ttttgcctac acagtcatag tgcatcgcat acattttgc    1080
tgcccgtaga gatcagaagg gagcattggg ttccctagga ctggaggcat gaaccacctt   1140
gtgggtgcag agaactgagc ctgggtcatc tcaaagcatc aggttcttct tgagtcatct   1200
cacttgccac ttctcccatt tactgatttt atctgtgtgc agacattcat ggcccagtcc   1260
acaggtggaa gtcagggaca acctatagga gtcagtcctc tccttctacc gtgtgagtcc   1320
ctggcctcaa actcaggttg tcgggcttca tagcaagagc ttctatttgt tgagccatct   1380
tgctagcccc accccatact atctttataa tatctgttta attaagacat tcataatgaa   1440
ttttattaac attcatcgtt atcccctta ccaattttac tatgtattaa ttgccacccc    1500
tttaaattta attacttcct tggctgggtt ttacaggaga gttccaggaa gctagatgga   1560
gagatggctc aacagtttag agcaacggct gttcttgcag aggacctagg ttcaagtcct   1620
ggcactcaga ggtggctcac aatcatctgt gacttcagtt ccaggggatc tgaagaattc   1680
ttctgggctc catgggcatc aactacacac ttggttcata gacatacatg ccagcaaatg   1740
attgatccat acatatgaaa taaaccataa acagaaaaaa aaaaggaagg tgagggaagg   1800
aaaaaaagtt taaaaaaagg aaaggaagga aggaagggan nnnnnnnnn nnnnnnnnn    1860
nnnnnnnnnn nnnnnnnnnn nnntctctc catactgaaa gatgtccaca atgactaagg    1920
gaattttttt taaaagacaa gcacaacgtt ttctagggat caaactctat ttgtgaggaa   1980
gactggtggt ttgaagatta catagcagag ttacatctaa catgagcgtg tttcccctgg   2040
atggaaggag tctgataact tgtctttctt tcttagttag catctcagag tcccccgcct   2100
cccttaacat ccttttttgca caccatcttt ttaggaaaat ggatcattta tgggggatgta  2160
gtgatttgta caagaatgtc ccctgtgggc tcagatattt gaatacttag ttcccagttg   2220
ggggagcttt tgtaggggagg ttgggaggca cagcctggca ggaggaagca tgctagcagc  2280
tttgagacta taaaccctca tctactacct tgttctcttt ctgcattgtg ctgtgtctga   2340
cactgtgaga ttcctgctcc cgatgccatg cctgcccgcc atgatagact cctagccctc   2400
tggaaaggta acctcagtga actctcttct ataagtttct ttgctcctgg tgttttatca   2460
ctgaaacgaa aaagcttgca gggaggtagg aggcagcctg tggcgttgat tcaatgcacc   2520
tggccttatc ctcggatgag atcggtcacc agtcaaaaac tgtgagcttg aaggtcttgg   2580
gtgcttaaca tctattttta caaatcttat ttagcaactt agaactgtga aatattggaa   2640
agctacttaa accttctaaa ctccctcctc cacactatga gaatgttaca ttttctattc   2700
agttattttt gagcagtaaa cagatgaatc aaggaatatg cccatcacat caagagtgct   2760
cctaaatgga cttgcttgtt attcatttac agtgtggccc cttgactttc atcggcactc   2820
ctagcagaaa acaaaatccg ccagatggag ctggagagat ggctcagctg ttaagaatac   2880
ttatccctac acaggccctg gagccagttc ccagcaccca cacggtggct cacaaccatc   2940
tgtaactcca gttctaggag acccgactcc ctcttctgtc tgaaaacacc aggcacgcgt   3000
gcggtctaca tacaaacatg aaagcaaaat acacacatta cataaataaa tcttaaaaaa   3060
```

```
tgattcgggg tgggggaagg aaaaaaaagg atgttagaaa atcgatgtaa ctgttttttc    3120
cttttgcaca gatctaagtt agggaaggag aacattctct taccatcgaa aataattgtt    3180
ttcattgccc ccaagtctgc taatagagct tgctacctte atggctgtcg taaggatgag    3240
gcaaagatgg acttcagctt tcagactgtg tctgctcaaa tgttggctac tcctgttttc    3300
tgaccccctt ctctggtgca atgtggactt tcaattaatt tccctgcatc ttttacatat    3360
ttgatttaaa aaatatttta ttttatgtaa ttgtatgtat atgcatgtca ataagcatat    3420
gtgtgtgtgt ttccatggaa accaaggcaa cagattttcc agagctgtag aaatgggctg    3480
tgagacgccc actgtgggtg ttcggaacca aactcgggtc ctgtggaaag acagcgagca    3540
cccataatgc agaggtatct ctcagatttt actttaaaat ttcaattttc tttttttttt    3600
ttaaagttcc aagtaactat aggaaagtac atgggtatat agatccccag taccaagatt    3660
cttcctttgc aggtagcaca acttggtttg tttcacataa agaatggaaa gtcattaaaa    3720
cactcatcac actgtaaagt agaattgaac tctgacagaa caagcgaagt gagtctgact    3780
tccaggtaac tgagccttct tttcctccta aagacacaag ccatacacag agtaaaataa    3840
acttgggcat ggtgagaagg aaacaacgca ggagggctag ccaagtctga gagtcgtgag    3900
tgtgctcggt ttataaacgg agcccacctt gccagcgagg tagtcacatg ctctgctaaa    3960
cagaaactta agaaaacact tacacgaagc aaacatgggg aagtgccatg caagcatgtg    4020
actgactggt ggcaatgacc gaaaccacag cagccactag aaaaggaagg gtagtgcgcc    4080
acactgtagt tgtgaaaatg aacttattca tttattttga aaaacgtgta agaagcaaag    4140
atgtcttctt tcccacctac ctttgcggca ggcgagcact tcctggaatt tataaagtgc    4200
gatctttctg gggacttctc ataacatttc ctactgctca tctatgtctg tgtcaaatag    4260
agaatgctct tgaacaagtg tgtgtgtgtg tgtgtgtgcg cgcgcacgcg cactcactcc    4320
tgctctgttg aggtccagtt ttgatggtcc cgccagaggt atatttgagt atcatttctc    4380
aagagcttca gctgggagac actgcctctt actggcctga aggtcactag ctgattcatc    4440
tccgttgggg ctggcgcgcc ttggggatcc tcctatctct ccttcccag tgctgggata    4500 acaaggttgg caccacatga gccttttaaa atgtgagttt ggaagctcaa acgcaggttt    4560
tcatgcttgc actgaaactt cacaagctga accgtctccc tctccttccc tctcttttt    4620 ccttttcttc ttccttttta aaacacatct tgtctttaaa aaaaaaaaaa ggcccaaaac    4680
aagtgtaaag tatttcccta tgtgtgtgga gggagggagt ataggaggct gatttcactg    4740
agatcctgtt aaatttgggt gccatagcca atcaaagacg catcgtttcc tctaagaatt    4800
ctaaatgggg cgattaccac gggcctgcag gttctggttt gtattagagg agacactgtc    4860
ttcttaagta aaacatagaa ggggaagtgt ccagaattgt aaataaggct tcgagagaag    4920
ccttgtctgg ccaccgggat ggagaagacc taccttcgcc tatccaggat ccatcgtccc    4980
tccctctacc cagatctgac agccctcctt ggctcttttg ctgaggtttg tttgagtttg    5040
ttttactctc tgcaagagaa gtttccttaa acattctacc ctgttcacaa gtaaatacac    5100
ctcttagcta agaggccaca cacccagggg gaacaccgat aaaagaacaa gccagaacc    5160 ttcagaacgc tgtcgatagg tacaccaagc agccttcata cggagttttc attcgtgagg    5220
agctgaatat acaacaaagc taatgtgagg cagaccaggc atgcctctgc taaatgagga    5280
tgcccacacc aaacatgccc aagatcttca gtataattt tattatatag attcgctatg    5340
tgttgacatg ttttatagt gaacctggat tttacaaacc ctcctggttt gccacctgct    5400
tctggcacca tacttgaggc ttaggcacgt gataaaggag catgcctgtt tccccccta    5460
```

```
tttttttttaa agaaaagcac catgttacat cattaatcat gcatatcagt gtagtttaga      5520
tccgatgtag agacaataat cttatctctt tgtctggctg aaagactgtc ctttaaacta      5580
tcattctaaa tgcatttggt ttttgccagg agtaaaacat gtcacaagat atttgttgtc      5640
atttcccagg cgtggaagga aaggaatgga aagaaaacca ggggtgaagg ctgctgttcc      5700
tctctagtcg ctacttgaag tctacatagc tggggggggg gggggactg ttcacatggg       5760 accggtttcc tctttgttcc tacactggcg cctctggcaa aaactctcc cttctcttcc      5820 ccccaagcat atcttggctg aaaggtcagc tctgaaaagg ggcctggcca aagttactgt      5880 agggggaccgt ggtcatggaa ctgggtaaac aaaagcactc tagcagccac tggaaaagga    5940 ccggggggctc ttctctgtgc atttgccctg gaaccctgac caccgccagc tccctgcatc     6000
tccttgctat gggttttctg gaccgaccca gccaggaagt tcacaaccga aatgtcttct     6060
agggctaatc aggtaacttc ggacgattta aagttgccag atggacgaga aaacagtaga    6120
ggcgttggca acctggataa gcgcctatct tctaattaaa acattcagac ggggcggggg     6180
atgcggtggc caaagcacca taaaacaaaa cttccaagta ctgaccaact cactgcaagt    6240
ttgtgccccg agtacatcta ggttcagggg ttcttgtctt catgctccca actgcgggcg    6300 gattttggt cccttgggac tttcagtgca gcggcgaaga gagttctgca cttgcaggct     6360
cctaatgagg gcgcagtggg cctcgtgttt ctggtgatgc ttcccaggtt gctggggca     6420 gcaagtgtct cagagcccat tactggctac attttacttc caccagaaac cgagctgcgt    6480
ccagatttgc tctcagatgc gacttgccgc ccggcacagt tccggggtag tgggggagtg   6540
ggcgtgggaa accgggaaac ccaaacctgg tatccagtgg ggggcgtggc cggacgcagg    6600
gagtccccac ccctcccggt aatgaccccg ccccccattcg ctagtgtgta gccggcgctc   6660
tctttctgcc ctgagtcctc aggaccccaa gagagtaagc tgtgtttcct tagatcgcgc   6720
ggaccgctac ccggcaggac tgaaagccca gactgtgtcc cgcagccggg ataacctggc   6780
tgacccgatt ccgcggacac cgctgcagcc gcggctggag ccagggcgcc ggtgccccgc   6840
gctctccccg gtcttgcgct gcgggggcgc ataccgcctc tgtgacttct ttgcgggcca   6900
gggacggaga aggagtctgt gcctgagaac tgggctctgt gcccagcgcg aggtgcagga   6960
tggagagcaa ggcgctgcta gctgtcgctc tgtggttctg cgtggagacc cgagccgcct   7020
ctgtgggtaa gaagcccact ctttagtagt aaggcggaga agtagggtgc gggcggagag   7080
tgggaataga agaggaccta actcgtagag ctctagagac cctcctccct tgggtgttct   7140
ttcacttacc aatggggaaa ctgaggttca aagactcttc cgaaatgact cagccaggat   7200
tctactctcc cccgggcatc ggttggagcg tgtcctgcgg agccgtcaca gcccctggcg   7260
ctaggtaggc aggagtggaa aggcggcctg agccggggca ggagatgctc ccactggcag   7320
gaacaggcgg tcaaacgctg ggaagccagc tcaagccaag cggcccggct ggcatcaatc   7380
actcggtgct gttgcccacc gccctagtgg ggggcaggga atccgcctct ggctccgctc   7440 cccttttagct ccagcgtgta agcgcacgga ctatgtgagg gtaggtctct tcatagagca  7500
acactttcct ccctcaactt tctttgatgc agaatgctat ttttgctggt aggaggaaga   7560
cgcggctttc tcttctgtga cagcttctcc aggtgtatta aactaaataa ctctccactt   7620
accgactcca aagcgctggt cctggggtaa actctgaaag tctcagaaac tcttgagctt   7680
ggcacctagt tataggtcac ttttcttgtt ttaaaatgcc ctctgcttca aggttaggcc   7740
cacactcgct cttgggcttt tgtgcaataa tttcccttcc cttcccttcc cttcccttcc   7800
```

```
cttcccttcc cttcccttcc cttcccttcc cttcccttcc cctcttcctt ttcctcctcc    7860
tcttcctcct ctatttctct gtcatttcct ttttgaagcc acagtttgca gatttccaat    7920
ctccacccat tggagaatgg agaatcagga aaaagaagt caattctgca gaaacattcc     7980
ttgcgcccta agagaatcgc atggcttaaa agcattggca ctgacatacg gcgccaagat   8040
cgcctgtcta gagctattga gttttcctca taatgacttg gttcatcagg ctagctccac    8100
cacgagtgcc ctcttgttcc tgagaaggcc gcactctccc cctttctggg aagagaaaga   8160
cagcctggaa catgtgcttg ccctgggttc catagagaag caagttgctt taaagcccag    8220
agaattccta gtgtagcagc ttaacagcgt cccgttctct gaataagatg gaggttgccc    8280
ttttggagtg tgtgacttgc ttaattggat tgggctataa ttggtgccat ccaagtctcg    8340
agacagagcc gctgttgttt ttccttctgg tctttgagcg ggaaggataa cagtgcacaa   8400
attaattaat gttggttatc ggatttgaac ataaagggc ttttattgta tagtagcata     8460
tgtacctctt gcagtcagaa tgagctgtct aaagaacaga acccaaactt gccgatgaaa   8520
atgaatgagg tttaataaag gcgatggatg agcattagtc actgatgtaa atctccagtt   8580
attgataacc tcattgactg gatttgattg cagacatgta ttggtatggg gcatcccttta  8640 aagatgagca tagccaacgt gcctgcactc taagagaatc tatggctgta tgttattaca   8700
gagacagttg agaagctctt agtggctctg gcgtgtagat cagcggtaga gcgctgaggc   8760
tctgcgctcg cttcctggca ctgaagaata aaggccattt actgtggtgg tgcagtgggc   8820
gcagtttgtg acgagttact actacatttt cctcacacat ctgcctgact aatgagttca   8880
tcagatgagc gtatccagtg attgtttgca ggttaatggt tctcagtcat gtttagaatc   8940
tacttatcaa acaaattgtt ttctcatttc ctgcttcttc tcaaacaaag taagattcca   9000
ttattgaaag gcttgtttaa gagcatttta actgcttgcc tatgttaggg acagtgactt    9060
atttcatatt gacaaatatt atgccgatta attgaatatg actacccagt tctatagctg   9120
tctcagggca gaccaagagc atctgtgatc cagtcacttt aaatgccatt taaaatgcat   9180
aatttgttgg tctaggaata aacacactgt aaagtttaga atcacggccc aaacacaagt   9240
ctttaacaat gccaactagc ttctgagatt cattaatgtc atttaattac caatgttttta  9300 aaaatatgtc attaattact aaatctatag ttgtaacagc aacacatgta catcttatta   9360
agttgggtat attcagggtg gcatagctgt agactattgc acatctgtgt tggtgagcca   9420
gtggagaact gcctcctggc tgttctcaga aggccacagt gtcacggcat tggctatttg   9480
ccttggctct ttgctaatac tttattgaca tggcctcatc ttcgttcacg ttcacttatt   9540
tgcccaacaa cgtcaatgcc agctgaggcc ttaggagtca tctgttctta gtcagtgcga   9600
attagaaagc ctggatgcct gcctgctatt aattagttat tcttctcttc tgagacagag   9660
tctcactgtg tggcccaggc tagtctcaaa cttgcggtcc atttgtctca ctcatcagaa   9720
tgctgggctt ccaggtgtgt gcaccacact aggtagctcc cgttttaagc taagagctgg   9780
aagatcctga tgtcctttac catggtgggc atgttacagg ttagttgact gaaaactagt    9840
tatctcgctg tgtaatgacc tgcagtggta tgtatctctc aagatgcttt tttgcatttc   9900
aatcagttag gtaacaagtt cttaagtctc cagcttggta ttggcatgag ctcagagctt   9960
tgattaatga gttgggaccc cctagctatt gctcattaga cttacactat ttttagtttt   10020
gctctgagtt tatgaatatg catgtatgca tgaacttggg agatattttt cttccccaat   10080
tccttttcct ccatttaaat gtgctgtctt tagaagccac tgcctcagct tctgcagctc   10140
agataccaaa ggaagtctgg tacacagcat gataaaagac aatgggacgg ggtcacagtg   10200
```

```
gctcccgtcc ctttcagggg tatggagacg agctgtagag agatgtctcc agggagtttt  10260
cattaatcag caatttagtc agatctgtgc atcctatgct ttacaagaaa tgtcagtggg  10320
cctgagatca tcagatggag gttcatcggg tttcaatgtc ccgtatcctt ttgtaagacc  10380
ttgaagttgg caacgcagga aaacaggaac tccaccctgg tgccgtgaat tgcagagctg  10440
ttgtgttggt ttgtgaccat ctgcccattc ttcctgttat gacagagctt gtgaacttta  10500
actgggactg gggcaaagtc aatcccacct ttatacaatg aattgctgaa gaggcctttt  10560
aaaacttgga gtgtgcattg tttatggaag ggctttccta ttggatccaa ctcttttcta  10620
atttgtttct aggtttgcct ggcgattttc tccatccccc caagctcagc acacagaaag  10680
acatactgac aattttggca aatacaaccc ttcagattac ttgcaggtaa ggattccttt  10740
ttgagccagc tttcctatgt gaaaggactc attgtttact gaggtcacaa caatttccac  10800
tattgcagaa gtataatagt attgttacaa ttgtttataa atcatgagac ttctaagaac  10860
ctatttaata atgaaacaat ggaaaagtc ttttcaaacc tttgtactct tttgctgagc  10920
cgttttcaac atgcacaaac atattacaca aatataacat acacaggaac acacatgaat  10980
gcatgggatg atgtgcctaa aactagcatg taattgatat tcacaattat tgataaatta  11040
gtaaagcaaa ggaattcctt atgaatagag ctaaaattct atccatgttc aagtcaccca  11100
gaatggcttc tggacatttt ttttttagc tgttttctac aagtgaaatt ctgcctgtat  11160
tagcaattta atatctagcc aataatattc ctgaccatat gtcctgttca gaccatgacc  11220
ttcataatct ggcttgatgt tctgggcttc ttttccctctt gccagcaaga tgtcacggtg  11280
ttgatgctgg ataaactgag aaacagaagt ttttcgcaag aagaggacct tgaattttgc  11340
ttttcccctg agagacaaga aaggaaactt agaggaggtg tagctgggag tgtggtcatt  11400
catgaaagac ctgtttgcag ggcagtgtgt tttgctgggg acagtaatga gcctagatcg  11460
tagtgccatc ccaagagagt gcttggtggc aaaaagagcc ctagcagctt gtggcagttg  11520
cctcatattt gaagaatact aagaggtccc ccgaataact cagggctagt gttgatcatt  11580
gcatgtggag agaatccaag cctcctatct agggtctaca aaagtaacca atgcccagtc  11640
tttgggggaa agcaaaacca gaaagcgatg atagcaggac ctgtttatt tcattaagtc  11700 atggcatttc cagagacttt gctcccccta ttctcagaca caaagcccac ttaagatctc  11760
cctctggaga ctgctgggaa catttcttaa gttctgaaaa aaccctggag tgattgggca  11820
cagacgatcc tgtcacttca tgtgagtgct aagctctttg ggtgatgact cagtgggtca  11880
cattgtttta ttcatattga ctaccttccg tttgctttgc ggagaatgga agctatagaa  11940
gtctgtttgg tgtggccctc acaaggcact gtgagcttct tctctctgtg tgctaacttc  12000
ttactctccc ttgcttatac ccacataggg actctggctt tgttgctgtt cttcaatgct  12060
tcagatgtgc cctgggtcct gtctgtcctt cacacttact gatgctgcct ggaatgctat  12120
tcctcccaat gtgcataggg ccagctcggt ccaaatcctc tctttctttt gcctcttttt  12180 tatttttcctt cacagtatca aatcaccaca gtttatgcaa caaactgaaa ctttaaaatt  12240
gtctgtctcc ttatattagt gataggttcc agaaaggcac tgatttttt tcttccctgg  12300 tgtacactgg gcaactactc taccactgag cgtgatatcc ttggtccctt aaaagttatc  12360
ctctgtcctt aataatgctt agcaatcata tttgcttaaa atatttattg aatgactgca  12420
ggaatgaatg aatgaatgag ctaacagaaa actcatgacc atgtgggtga tttccgaaac  12480
agagtgtgag atctttggtg gcatgtcctt gtagactgtc tgccaccagt atctatcatc  12540
```

-continued

```
ttgaaggtga ctattgagta gtttatatgc atgtgaaaaa ccaaaccttc tattctctta    12600
ctcatagcct ctcttaatca tagccctgtg gcatggagtg taccattgat atcttcctgg    12660 aatactttt cagggacag cgggacctgg actggctttg gcccaatgct cagcgtgatt    12720
ctgaggaaag ggtattggtg actgaatgcg gcggtggtga cagtatcttc tgcaaaacac    12780
tcaccattcc cagggtggtt ggaaatgata ctggagccta caagtgctcg taccgggacg    12840
tcgac                                                                12845

<210> SEQ ID NO 2
<211> LENGTH: 31
<212> TYPE: DNA
<213> ORGANISM: Artificial sequence
<220> FEATURE:
<223> OTHER INFORMATION: Flk-1upstream primer

<400> SEQUENCE: 2
ggggtaccga attctaaatg gggcgattac c                                   31

<210> SEQ ID NO 3
<211> LENGTH: 27
<212> TYPE: DNA
<213> ORGANISM: Artificial sequence
<220> FEATURE:
<223> OTHER INFORMATION: Flk-1 upstream primer

<400> SEQUENCE: 3
gtggtaccca aacactcaac accactg                                        27

<210> SEQ ID NO 4
<211> LENGTH: 26
<212> TYPE: DNA
<213> ORGANISM: Artificial sequence
<220> FEATURE:
<223> OTHER INFORMATION: Flk-1 upstream primer

<400> SEQUENCE: 4
tcggtaccga cccagccagg aagttc                                         26

<210> SEQ ID NO 5
<211> LENGTH: 29
<212> TYPE: DNA
<213> ORGANISM: Artificial sequence
<220> FEATURE:
<223> OTHER INFORMATION: Flk-1 downstream primer

<400> SEQUENCE: 5
ttgctaagct tcctgcacct cgcgctggg                                      29

<210> SEQ ID NO 6
<211> LENGTH: 27
<212> TYPE: DNA
<213> ORGANISM: Artificial sequence
<220> FEATURE:
<223> OTHER INFORMATION: Flk-1 intron primer

<400> SEQUENCE: 6
agggatccac tctttagtag taaggcg                                        27

<210> SEQ ID NO 7
<211> LENGTH: 21
<212> TYPE: DNA
<213> ORGANISM: Artificial sequence
<220> FEATURE:
<223> OTHER INFORMATION: Flk-1 intron primer
```

```
<400> SEQUENCE: 7
acctcgagac ttggatggca c                                              21

<210> SEQ ID NO 8
<211> LENGTH: 21
<212> TYPE: DNA
<213> ORGANISM: Artificial sequence
<220> FEATURE:
<223> OTHER INFORMATION: Flk-1 intron primer

<400> SEQUENCE: 8
gggctataat tggtgccatc c                                              21

<210> SEQ ID NO 9
<211> LENGTH: 21
<212> TYPE: DNA
<213> ORGANISM: Artificial sequence
<220> FEATURE:
<223> OTHER INFORMATION: Flk-1 intron primer

<400> SEQUENCE: 9
ggatggagaa aatcgccagg c                                              21

<210> SEQ ID NO 10
<211> LENGTH: 22
<212> TYPE: DNA
<213> ORGANISM: Artificial sequence
<220> FEATURE:
<223> OTHER INFORMATION: Flk-1 intron primer

<400> SEQUENCE: 10
gtgtgcattg tttatggaag gg                                             22

<210> SEQ ID NO 11
<211> LENGTH: 22
<212> TYPE: DNA
<213> ORGANISM: Artificial sequence
<220> FEATURE:
<223> OTHER INFORMATION: Flk-1 intron primer

<400> SEQUENCE: 11
catagacata aacagtggag gc                                             22

<210> SEQ ID NO 12
<211> LENGTH: 25
<212> TYPE: DNA
<213> ORGANISM: Artificial sequence
<220> FEATURE:
<223> OTHER INFORMATION: -258fw primer

<400> SEQUENCE: 12
atggtaccca ggttgctggg ggcag                                          25

<210> SEQ ID NO 13
<211> LENGTH: 21
<212> TYPE: DNA
<213> ORGANISM: Artificial sequence
<220> FEATURE:
<223> OTHER INFORMATION: LacRev primer

<400> SEQUENCE: 13
tggtgccgga aaccaggcaa a                                              21

<210> SEQ ID NO 14
```

```
<211> LENGTH: 20
<212> TYPE: DNA
<213> ORGANISM: Artificial sequence
<220> FEATURE:
<223> OTHER INFORMATION: LacZP1 primer

<400> SEQUENCE: 14
atcctctgca tggtcaggtc                                                   20

<210> SEQ ID NO 15
<211> LENGTH: 18
<212> TYPE: DNA
<213> ORGANISM: Artificial sequence
<220> FEATURE:
<223> OTHER INFORMATION: LacZP2 primer

<400> SEQUENCE: 15
cgtggcctga ttcattcc                                                     18

<210> SEQ ID NO 16
<211> LENGTH: 33
<212> TYPE: DNA
<213> ORGANISM: Artificial sequence
<220> FEATURE:
<223> OTHER INFORMATION: tk5' promoter primer

<400> SEQUENCE: 16
gggaattcac catgagttct gaacgtcgaa aag                                    33

<210> SEQ ID NO 17
<211> LENGTH: 59
<212> TYPE: DNA
<213> ORGANISM: Artificial sequence
<220> FEATURE:
<223> OTHER INFORMATION: tk3' promoter primer

<400> SEQUENCE: 17
aagcggccgc tcatttatcg tcatcgtcct tgtaatcgtt aacttgatcc aaagctctg        59

<210> SEQ ID NO 18
<211> LENGTH: 32
<212> TYPE: DNA
<213> ORGANISM: Artificial sequence
<220> FEATURE:
<223> OTHER INFORMATION: HIF Start primer

<400> SEQUENCE: 18
gggaattcac cacaatgaca gctgacaagg ag                                     32

<210> SEQ ID NO 19
<211> LENGTH: 64
<212> TYPE: DNA
<213> ORGANISM: Artificial sequence
<220> FEATURE:
<223> OTHER INFORMATION: HIF Flag Stop primer

<400> SEQUENCE: 19
aagcggccgc tcatttatcg tcatcgtcct tgtaatcgtt ggtggcctgg tccagagctc       60
tgag                                                                    64

<210> SEQ ID NO 20
<211> LENGTH: 29
<212> TYPE: DNA
<213> ORGANISM: Artificial sequence
<220> FEATURE:
<223> OTHER INFORMATION: HRF START primer
```

-continued

```
<400> SEQUENCE: 20
ccggtaccca aaccccgccc agcgtcttg                                          29

<210> SEQ ID NO 21
<211> LENGTH: 30
<212> TYPE: DNA
<213> ORGANISM: Artificial sequence
<220> FEATURE:
<223> OTHER INFORMATION: HRF rev primer

<400> SEQUENCE: 21
ccgacaagct tggtcgctcg gtgttcgagg                                         30

<210> SEQ ID NO 22
<211> LENGTH: 511
<212> TYPE: DNA
<213> ORGANISM: Mus musculus

<400> SEQUENCE: 22
aaatgtgctg tctttagaag ccactgcctc agcttctgca gctcagatac caaaggaagt        60
ctggtacaca gcatgataaa agacaatggg acggggtcac agtggctccc gtccctttca       120
ggggtatgga gacgagctgt agagagatgt ctccagggag ttttcattaa tcagcaattt       180
agtcagatct gtgcatccta tgctttacaa gaaatgtcag tgggcctgag atcatcagat       240
ggaggttcat cgggtttcaa tgtcccgtat ccttttgtaa gaccttgaag ttggcaacgc       300
aggaaaacag gaactccacc ctggtgccgt gaattgcaga gctgttgtgt tggtttgtga       360
ccatctgccc attcttcctg ttatgacaga gcttgtgaac tttaactggg actggggcaa       420
agtcaatccc acctttatac aatgaattgc tgaagaggcc ttttaaaact tggagtgtgc       480
attgtttatg gaagggcttt cctattggat c                                      511
```